US009243034B2

(12) United States Patent
Eldar-Finkelman et al.

(10) Patent No.: US 9,243,034 B2
(45) Date of Patent: Jan. 26, 2016

(54) GLYCOGEN SYNTHASE KINASE-3 INHIBITORS

(75) Inventors: Hagit Eldar-Finkelman, Shoham (IL); Avital Licht-Murava, Tel-Aviv (IL); Batya Plotkin, Rishon-LeZion (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 13/981,668

(22) PCT Filed: Jan. 26, 2012

(86) PCT No.: PCT/IB2012/050373
§ 371 (c)(1), (2), (4) Date: Jul. 25, 2013

(87) PCT Pub. No.: WO2012/101599
PCT Pub. Date: Aug. 2, 2012

(65) Prior Publication Data

US 2013/0310303 A1 Nov. 21, 2013

Related U.S. Application Data

(60) Provisional application No. 61/436,640, filed on Jan. 27, 2011.

(51) Int. Cl.

| | |
|---|---|
| ***A61K 38/08*** | (2006.01) |
| ***A61K 38/10*** | (2006.01) |
| ***C07K 7/06*** | (2006.01) |
| ***C07K 7/08*** | (2006.01) |
| ***C12N 9/12*** | (2006.01) |

(Continued)

(52) U.S. Cl.
CPC . *C07K 7/08* (2013.01); *A61K 38/08* (2013.01); *A61K 38/10* (2013.01); *C07K 7/06* (2013.01); *C12N 9/12* (2013.01); *C12N 9/1205* (2013.01); *C12Q 1/485* (2013.01); *C12Y 207/11001* (2013.01); *A61K 38/00* (2013.01)

(58) Field of Classification Search
None
See application file for complete search history.

(56) References Cited

U.S. PATENT DOCUMENTS 6,780,625 B2 8/2004 Eldar-Finkelman
7,378,432 B2 5/2008 Eldar-Finkelman et al.
7,446,092 B2 11/2008 Eldar-Finkelman (Continued)

FOREIGN PATENT DOCUMENTS

WO WO 01/49709 7/2001
WO WO 2004/052404 6/2004

(Continued)

OTHER PUBLICATIONS

Donella-Deana et al. Dephosphorylation of phosphopeptides by calcineurin (protein phosphatase 2B). European Journal of Biochemistry. 1994, vol. 219, Nos. 1-2, pp. 109-117.*

(Continued)

*Primary Examiner* — Jeffrey E Russel

(57) ABSTRACT

Novel peptide inhibitors of GSK-3, compositions containing same and uses thereof are disclosed. The novel peptide inhibitors are substrate-competitive inhibitors and have an amino acid sequence designed so as to bind to a defined binding site subunit in GSK-3. Also disclosed are GSK-3 substrate competitive inhibitors which bind to the defined binding site subunit in the enzyme. Also disclosed are mutants of GSK-3 and uses thereof for identifying a putative GSK-3 substrate competitive inhibitor.

55 Claims, 6 Drawing Sheets

(51) Int. Cl.
*C12Q 1/48* (2006.01)
*A61K 38/00* (2006.01)

(56) References Cited

U.S. PATENT DOCUMENTS

2009/0068684 A1* 3/2009 Moritz et al. ................ 435/7.23
2011/0059463 A1* 3/2011 Moritz et al. .................. 435/7.1
2011/0150887 A1* 6/2011 Rincon et al. .............. 424/139.1
2013/0303441 A1 11/2013 Eldar-Finkelman et al.

FOREIGN PATENT DOCUMENTS

WO WO 2005/000192 1/2005
WO WO 2012/101599 8/2012
WO WO 2012/101601 8/2012

OTHER PUBLICATIONS

Communication Relating to the Results of the Partial International Search Dated May 30, 2012 From the international Searching Authority Re. Application No. PCT/IB2012/050373.

International Search Report and the Written Opinion Dated Nov. 9, 2012 From the International Searching Authority Re. Application No. PCT/IB2012/050373.

International Search Report and the Written Opinion Dated Jun. 11, 2012 From the International Searching Authority Re. Application No. PCT/IB2012/050376.

Bertrand et al. "Structural Characterization of the GSK-3β Active Site Using Selective and Non-Selective ATP-Mimetic Inhibitors", The Journal of Molecular Biology, 333: 393-407, 2003.

Chen et al. "Glycogen Synthase Kinase 3β (GSK3β) Mediates 6-Hydroxydopamine-Induced Neuronal Death", The FASEB Journal, p. 1-26, May 7, 2004.

Dajani et al. "Crystal Structure of Glycogen Synthase Kinase 3 Beta: Structural Basis for Phosphate-Primed Substrate Specificity and Autoinhibition", Cell, 105: 721-732, 2001.

Fiol et al. "Formation of Protein Kinase Regognition Sites by Covalent Modification of Substrate. Molecular Mechanism for the Synergistic Action of Casein Kinase II and Glycogen Synthase Kinase 3", The Journal of Biological Chemistry, 262(29): 14042-14048, 1987.

Ilouz et al. "Identification of Novel Glycogen Synthase Kinase-3β Substrate-Interacting Residues Suggests a Common Mechanism for Substrate Recognition", The Journal of Biological Chemistry, 281(41): 30621-30630, Oct. 13, 2006.

Ilouz et al. "New Insights Into Autoinhibition Mechanism of Glycogen Synthase Kinase-3Beta", Journal of Molecular Biology, XP025536484, 383(5): 999-1007, Nov. 28, 2008.

Kaidanovich-Beilin et al. "Long-Term Treatment With Novel Glycogen Synthase Kinase-3 Inhibitors Improves Glucose Homeostasis in Ob/Ob Mice: Molecular Characterization in Liver and Muscle", The Journal of Pharmacology and Experimental Therapeutics, 316(1): 17-24, 2006.

Kaidanovich-Beilin et al. "Rapid Antidepressive-Like Activity of Specific Glycogen Synthese Kinase-3 Inhibitor and Its Effect on β-Catenin in Mouse Hippocampus", Biological Psychiatry, 55: 781-784, 2004.

Kim et al. "Essential Roles for GSK-3s and GSK-3-Primed Substrates in Neurotrophin-Induced and Hippocampal Axon Growth", Neuron, 52(6): 981-996, Dec. 21, 2006.

Kowalsman et al. "Combining Interface Core and Whole Interface Descriptors in Postscan Processing of Protein-Protein Docking Models", Proteins, 77: 297-318, 2009.

Liberman et al. "Coordinated Phosphorylation of Insulin Receptor Substrate-1 by Glycogen Synthase Kinase-3 and Protein Kinase CβII in the Diabetic Fat Tissue", American Journal of Physiology, Endocrinology and Metabolism, 294(6): E1169-E1177, 2008.

Liberman et al "Serine 332 Phosphorylation of Insulin Receptor Substrate-1 by Glycogen Synthase Kinase-3 Attenuates Insulin Signaling", The Journal of Biological Chemistry, 280(6): 4422-4428, Feb. 11, 2005.

Licht-Murava et al. "Elucidating Substrate and Inhibitor Binding Sites on the Surface of GSK-3β and the Refinement of a Competitive Inhibitor", The Journal of Biological Chemistry, 408(2): 366-378, Apr. 25, 2011.

Palomo et al. "5-Imino-1,2,4-Thiadiazoles: First Small Molecules as Substrate Competitive Inhibitors of Glycogen Synthase Kinase 3", Journal of Medicinal Chemistry, 55(4): 1645-1661, Feb. 23, 2012.

Plotkin et al. "Insulin Mimetic Action of Synthetic Phosphorylated Peptide Inhibitors of Glycogen Synthase Kinase-3", Journal of Pharmacology and Experimental Therapeutics, 305(3): 974-980, 2003.

Rao et al. "Glycogen Synthase Kinase 3 Inhibition Improves Insulin-Stimulated Glucose Metabolism But Not Hypertension in High-Fat-Fed C57BL/6J Mice", Diabetologia, 50: 452-460, 2007.

Shapira et al. "Role of Glycogen Synthase Kinase-3Beta in Early Depressive Behavior Induced by Mild Traumatic Brain Injury", Molecular and Cellular Neuroscience, 34: 571-577, 2007.

Ter Haar et al. "Structure of GSK-3 Beta Reveals a Primed Phosphorylation Mechanism", Nature Structural Biology, 8(7): 593-596, 2001.

Woodgett et al. "Multisite Phosphorylation of Glycogen Synthase. Molecular Basis for the Substrate Specificity of Glycogen Synthase Kinase-3 and Casein Kinase-II (Glycogen Synthase Kinase-5)", Biochimica et Biophysica Acta, 788(3): 339-347, Aug. 14, 1984.

Communication Pursuant to Article 94(3) EPC Dated Mar. 18, 2015 From the European Patent Office Re. Application No. 12705426.0.

Czernik et al. "Production of Phosphorylation State-Specific Antibodies", Methods in Enzymology, XP002926234, 201: 264-283, 1991.

Otvos Jr. et al. "Glycosylation of Synthetic Peptides Breaks Helices. Phosphorylation Results in Distorted Structure", International Journal of Peptide and Protein Research, 38: 476-482, 1991.

Titanji et al. "Activity of Rat-Liver Phosphoprotein Phosphatase on Phosphopeptides Formed in the Cyclic AMP-Dependent Protein Kinase Reaction", FEBS Letters, XP025615084, 78(1): 86-90, Jun. 1977.

Titanji et al. "Phosphopeptide Substrates of a Phosphoprotein Phosphatase From Rat Liver", The Journal of Biological Chemistry, 255(23): 11339-11343, Dec. 10, 1980.

Official Action Dated Sep. 10, 2015 From the U.S. Appl. No. 13/982,300.

Sugden et al. "Glycogen Synthase Kinase 3 (GSK3) in the Heart: A Point of Integration in Hypertrophic Signalling and a Therapeutic Target?A Critical Analysis ", British Journal of Pharmacology 153: 137-153, 2008.

* cited by examiner

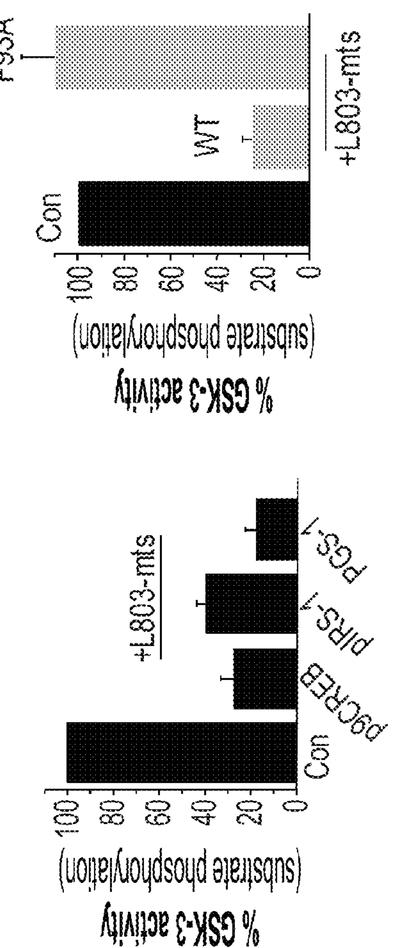
FIG. 2A
FIG. 2B
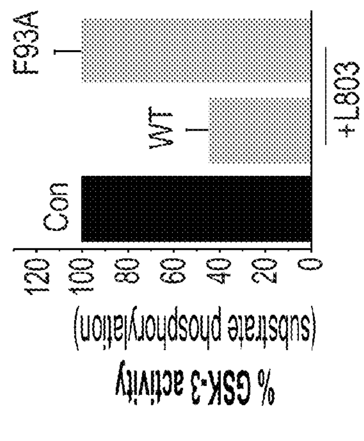
FIG. 2C
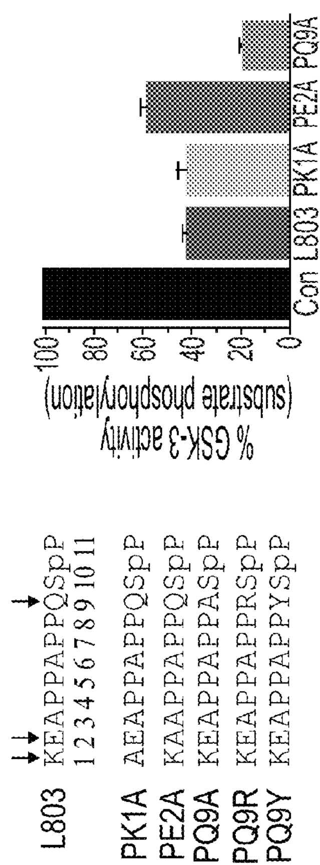
FIG. 3A
FIG. 3B
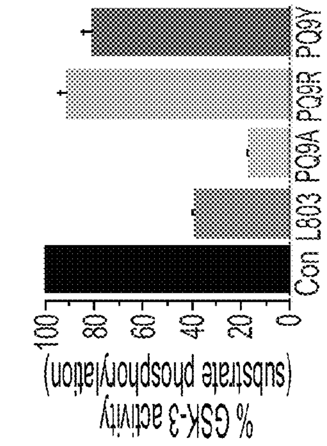
FIG. 3C PQ9P- KEAPPAPPPSpP L803 KEAPPAPPQSpP PQ9P KEAPPAPPPSpP PQ9A KEAPPAPPASpP

GLYCOGEN SYNTHASE KINASE-3 INHIBITORS

RELATED APPLICATIONS

This application is a National Phase of PCT Patent Application No. PCT/IB2012/050373 having International filing date of Jan. 26, 2012, which claims the benefit of priority under 35 USC §119(e) of U.S. Provisional Patent Application No. 61/436,640 filed on Jan, 27, 2011. The contents of the above applications are all incorporated by reference as if fully set forth herein in their entirety.

SEQUENCE LISTING STATEMENT

The ASCII file, entitled 56961SequenceListing.txt, created on Jun. 27, 2013, comprising 40,128 bytes, submitted concurrently with the filing of this application is incorporated herein by reference.

FIELD AND BACKGROUND OF THE INVENTION

The present invention, in some embodiments thereof, relates to novel glycogen synthase kinase-3 (GSK-3) inhibitors and, more particularly, but not exclusively, to novel substrate-competitive inhibitors of glycogen synthase kinase-3 (GSK-3) and to the use of such inhibitors in the treatment of biological conditions associated with GSK-3 activity.

Protein kinases and phosphorylation cascades are essential for life and play key roles in the regulation of many cellular processes including cell proliferation, cell cycle progression, metabolic homeostasis, transcriptional activation and development. Aberrant regulation of protein phosphorylation underlies many human diseases, and this has prompted the development and design of protein kinase inhibitors. Most of the protein kinase inhibitors developed so far compete with ATP for its binding site. These inhibitors, although often very effective, generally show limited specificity due to the fact that the ATP binding site is highly conserved among protein kinases.

Other sites, such as the substrate's binding site, show more variability in their shape and amino acid compositions and may serve as favorable sites for drug design. Understanding of substrate recognition and specificity is thus essential for development of substrate competitive inhibitors. This knowledge, however, is limited by the scarce amount of structural data regarding substrate binding.

Glycogen synthase kinase-3 (GSK-3) is a constitutively active serine/threonine kinase that modulates diverse cellular functions including metabolism, cell survival and migration, neuronal signaling and embryonic development. Deregulation of GSK-3 activity has been implicated in the pathogenesis of human diseases such as, for example, type-2 diabetes, neurodegenerative disorders and psychiatric disorders. Selective inhibition of GSK-3 is thought to be of therapeutic value in treating these disorders [Bhat et al. (2004). *J. Neurochem.* 89, 1313-7; Cohen, P. & Goedert, M. (2004). *Nat. Rev. Drug Discov.* 3, 479-87; Meijer et al. (2004) *Trends Pharmacol Sci* 25, 471-80; Eldar-Finkelman et al. *Biochim Biophys Acta* 1804, 598-603; Martinez, A. & Perez, D. I. (2008) *J. Alzheimers Dis.* 15, 181-91].

Recently, it has been found that GSK-3 is also involved in the pathogenesis of cardiovascular diseases [Cheng et al. 2010 *J. Mol Cell Cardiol*, in press; Kerkela et al. 2008, *J. Clin. Invest.* 118:3609-18], of malaria and trypanosomiasis [Droucheau et al. 2004, *BBRC,* 1700:139-140; Ojo et al. 2008, *Antimicrob Agents Chemother,* 37107-3717], and in stem cell maintenance or differentiation [Wray et al. 2010 *Biochem Soc Trans* 1027-32].

In view of the wide implication of GSK-3 in various signaling pathways, development of specific inhibitors for GSK-3 is considered both promising and important regarding various therapeutic interventions as well as basic research.

Some mood stabilizers were found to inhibit GSK-3. However, while the inhibition of GSK-3 both by lithium chloride (LiCl) (WO 97/41854) and by purine inhibitors (WO 98/16528) has been reported, these inhibitors are not specific for GSK-3. In fact, it was shown that these drugs affect multiple signaling pathways, and inhibit other cellular targets, such as inositol monophosphatase (IMpase) and histone deacetylases.

Similarly, an engineered cAMP response element binding protein (CREB), a known substrate of GSK-3, has been described (Fiol et al, 1994), along with other potential GSK-3 peptide inhibitors (Fiol et al, 1990). However, these substrates also only nominally inhibit GSK-3 activity.

Other GSK-3 inhibitors have been reported. Two structurally related small molecules SB-216763 and SB-415286 (GlaxoSmithKline Pharmaceutical) that specifically inhibited GSK-3 were developed and were shown to modulate glycogen metabolism and gene transcription as well as to protect against neuronal death induced by reduction in PI3 kinase activity (Cross et al., 2001; Coghlan et al., 2000). Another study indicated that Induribin, the active ingredient of the traditional Chinese medicine for chronic myelocytic leukemia, is a GSK-3 inhibitor. However, Indirubin also inhibits cyclic-dependent protein kinase-2 (CDK-2) (Damiens et al., 2001). These GSK-3 inhibitors are ATP competitive and were identified by high throughput screening of chemical libraries. It is generally accepted that a major drawback of ATP-competitive inhibitors is their limited specificity (see, for example, Davies et al., 2000).

The present inventors have previously reported of a novel class of substrate competitive inhibitors for GSK-3 [Plotkin et al. (2003) *J. Pharmacol. Exp. Ther.,* 974-980], designed based on the unique substrate-recognition motif of GSK-3 that includes a phosphorylated residue (usually serine) in the context of SXXXS(p) (where S is the target serine, S(p) is phosphorylate serine and X is any amino acid) [see also Woodgett & Cohen (1984) *Biochim. Biophys. Acta.* 788, 339-47; Fiol et al. (1987) *J. Biol. Chem.* 262, 14042-8]. Structural studies of GSK-3β identified a likely docking site for the phosphorylated residue; it is a positively charged binding pocket composed of Arg96, Arg180, and Lys205 [Dajani et al. (2001) *Cell* 105, 721-32; ter Haar et al. (2001) *Nature Structural Biology* 8, 593-6].

The short phosphorylated peptides patterned after the GSK-3 substrates behaved as substrate competitive inhibitors (Plotkin et al., 2003, supra), with the L803 peptide, KEAPPAPPQS(p)P (SEQ ID NO:4), derived from the substrate heat shock factor-1 (HSF-1) showing the best inhibition activity of those evaluated. An advanced version of L803, the cell permeable peptide L803-mts, was shown to promote beneficial biological activities in conditions associated with diabetes, neuron growth and survival, and mood behavior [Kaidanovich-Beilin & Eldar-Finkelman (2005) *J. Pharmacol. Exp. Ther.* 316:17-24; Rao et al. (2007) *Diabetologia* 50, 452-60; Kim et al. (2006) *Neuron* 52, 981-96; Chen et al. (2004) *Faseb J* 18, 1162-4; Kaidanovich-Beilin et al. (2004) *Biol. Psychiatry.* 55:781-4; Shapira et al. (2007) *Mol. Cell Neurosci.* 34, 571-7].

While further focusing on substrate recognition of GSK-3, three positions in the vicinity of the catalytic site (Phe67 in the P-loop, Gln89 and Asn95) were identified as important for GSK-3 substrates binding [Ilouz et al. (2006) *J. Biol. Chem.* 281, 30621-30].

Additional background art includes U.S. Pat. Nos. 6,780,625 and 7,378,432; WO 2004/052404 and WO 2005/000192; WO 01/49709; Liberman, Z. & Eldar-Finkelman, H. (2005) *J. Biol. Chem.* 280, 4422-8; Liberman et al. (2008) *Am. J. Physiol. Endocrinol. Metab.* 294, E1169-77; Bertrand et al. (2003) *J. Mol. Biol.* 333, 393-407; Licht-Murava et al., *J. Mol. Biol.* (2011) 408, 366-378; and Palomo et al. *J. Med. Chem.* (2012) as published on wwwdotpubsdotacsdotorg as "Just Accepted Manuscript" on Jan. 18, 2012.

SUMMARY OF THE INVENTION

According to an aspect of some embodiments of the present invention there is provided a peptide having the amino acid sequence I:

$$[Yn \ldots Y_1]ZX_1X_2X_3S(p)[W_1 \ldots Wm] \quad (I)$$

wherein, m equals 1 or 2;

n is 3, 4, 5, 6 or 7, such that the peptide consists of 10 to 13 amino acid residues;

S(p) is a phosphorylated serine residue or a phosphorylated threonine residue;

Z is any amino acid residue excepting serine residue or threonine residue;

$X_1$, $X_2$, $Y_1$-Yn and $W_1$-Wm are each independently any amino acid residue; and $X_3$ is a hydrophobic amino acid residue.

According to some embodiments of the present invention, $X_3$ is selected from the group consisting of a proline residue and an alanine residue.

According to some embodiments of the present invention, $X_3$ is a proline residue.

According to some embodiments of the present invention, each of $X_1$, $X_2$ and $X_3$ is a hydrophobic amino acid residue.

According to some embodiments of the present invention, each of $X_1$, $X_2$ and $X_3$ is independently selected from the group consisting of a proline residue and an alanine residue.

According to some embodiments of the present invention, $X_1$ and $X_2$ are each a proline residue.

According to some embodiments of the present invention, S(p) is a phosphorylated serine.

According to some embodiments of the present invention, Z is an alanine residue.

According to some embodiments of the present invention, m is 1 and $W_1$ is a proline residue.

According to some embodiments of the present invention, n is 5.

According to some embodiments of the present invention, $Y_1$-$Y_5$ has the amino acid sequence Lys-Glu-Ala-Pro-Pro (SEQ ID NO:48).

According to some embodiments of the present invention, the peptide has an amino acid sequence selected from the group of amino acid sequences as set forth in SEQ ID NOS: 11-13 and 16.

According to some embodiments of the present invention, the peptide is consisting of the amino acid sequence as set forth in SEQ ID NO:16.

According to some embodiments of the present invention, any of the peptides described herein further comprises a hydrophobic moiety attached thereto.

According to some embodiments of the present invention, the hydrophobic moiety is selected from the group consisting of a fatty acid and a fatty acid attached to an amino acid residue.

According to some embodiments of the present invention, the fatty acid is myristic acid.

According to some embodiments of the present invention, the peptide consists of the amino acid sequence as set forth in SEQ ID NO:17.

According to an aspect of some embodiments of the present invention there is provided a pharmaceutical composition comprising, as an active ingredient, the peptide as described herein, and a pharmaceutically acceptable carrier.

According to some embodiments of the present invention, the pharmaceutical is packaged in a packaging material and identified in print, on or in the packaging material, for use in inhibiting an activity of GSK-3.

According to some embodiments of the present invention, the pharmaceutical composition is packaged in a packaging material and identified in print, on or in the packaging material, for use in the treatment of a biological condition associated with GSK-3 activity.

According to an aspect of some embodiments of the present invention there is provided a peptide as described herein, for use in inhibiting an activity of GSK-3.

According to an aspect of some embodiments of the present invention there is provided a peptide as described herein for use in the treatment of a biological condition associated with GSK-3 activity.

According to an aspect of some embodiments of the present invention there is provided a method of inhibiting an activity of GSK-3, the method comprising contacting cells expressing GSK-3 with an effective amount of the peptide as described herein.

According to an aspect of some embodiments of the present invention there is provided a use of the peptide as described herein in the manufacture of a medicament for inhibiting an activity of GSK-3 activity.

According to some embodiments of the invention, the activity is a phosphorylation activity and/or an autophosphorylation activity.

According to an aspect of some embodiments of the present invention there is provided a method of treating a biological condition associated with GSK-3 activity, the method comprising administering to a subject in need thereof a therapeutically effective amount of the peptide as described herein.

According to an aspect of some embodiments of the present invention there is provided a use of the peptide as described herein in the manufacture of a medicament for treating a biological condition associated with GSK-3 activity.

According to some embodiments of the invention, the biological condition is associated with overexpression of GSK-3.

According to some embodiments of the invention, the biological condition is selected from the group consisting of obesity, non-insulin dependent diabetes mellitus, an insulin-dependent condition, an affective disorder, a neurodegenerative disease or disorder, a psychotic disease or disorder, a cardiovascular disease or disorder, a condition associated with a pathogenic parasite, and a condition treatable by stem cell transplantation.

According to an aspect of some embodiments of the present invention there is provided a GSK-3 substrate competitive inhibitor capable of interacting with at least one amino acid within the catalytic binding site of a GSK-3 enzyme, the at least one amino acid comprising a phenylalanine residue at position 93, or an equivalent thereof of the GSK-3 enzyme.

According to some embodiments of the invention, the GSK-3 inhibitor is capable of interacting with at least one additional amino acid within the catalytic binding site of a GSK-3 enzyme.

According to some embodiments of the invention, the GSK-3 inhibitor is selected from the group consisting of a peptide, a polypeptide and an organic small molecule.

According to an aspect of some embodiments of the present invention there is provided a method of identifying a putative substrate competitive inhibitor of GSK-3, the method comprising screening a plurality of substances for a substance capable of interacting with a phenylalanine residue at position 93, or an equivalent thereof, within a catalytic binding site of GSK-3.

According to some embodiments of the invention, the method is comprising screening the plurality of substances for a substance which exhibits inhibition of at least 20% of an activity of a wild-type GSK-3 enzyme and which exhibits inhibition of less than 20% of the activity of a mutated GSK-3 enzyme, the mutated GSK-3 enzyme comprising an amino acid substitution with respect to position Phe93, or an equivalent thereof, of a corresponding wild-type GSK3 enzyme.

According to some embodiments of the invention, the screening comprises:

determining the activity of the wild-type GSK-3 enzyme in the presence and absence of each of the substances, thereby determining a level of inhibition of the activity of the wild-type GSK-3 enzyme exhibited by each of the substances;

determining the activity of the mutated GSK-3 enzyme in the presence and absence of each of the substances, thereby determining a level of inhibition of the activity of the mutated GSK-3 enzyme exhibited by each of the substances; and comparing the levels of inhibition.

According to some embodiments of the invention, the activity is phosphorylation.

According to some embodiments of the invention, the screening comprises computationally screening the plurality of substances for a substance capable of interacting with a phenylalanine residue at position 93, or an equivalent amino acid thereof, within a set of atomic structural coordinates defining a three-dimensional atomic structure of a GSK-3 enzyme.

According to some embodiments of the invention, the computationally screening is for a substance that is further capable of interacting with at least one additional amino acid within the catalytic binding site of the GSK-3.

According to an aspect of some embodiments of the present invention there is provided an isolated polypeptide comprising an amino acid sequence of a mutated GSK-3 enzyme, wherein an amino acid sequence of the mutated GSK-3 enzyme comprises at least one amino acid substitution with respect to position Asp90, Lys91, Arg92, Phe93 and/or Lys94 of a corresponding wild-type GSK3 enzyme.

According to some embodiments of the invention, theta least one amino acid substitution is with respect to position Asp90, Arg92, Phe93 and/or Lys94 of the corresponding wild-type GSK-3.

According to some embodiments of the invention, theta least one amino acid substitution is with respect to position Phe93 of the corresponding wild-type GSK-3.

According to some embodiments of the invention, the amino acid substitution comprises an alanine substitution.

According to some embodiments of the invention, the mutated GSK-3 enzyme comprises an amino acid sequence selected from the group consisting of the amino acid sequences set forth in SEQ ID NOS:6-10.

According to some embodiments of the invention, the mutated GSK-3 enzyme comprises an amino acid sequence as set forth in SEQ ID NO:9.

According to an aspect of some embodiments of the present invention there is provided a polynucleotide encoding the polypeptide of any of claims 39-44.

According to an aspect of some embodiments of the present invention there is provided a nucleic acid construct comprising the polynucleotide of claim 45.

According to an aspect of some embodiments of the present invention there is provided a host cell system comprising the nucleic acid construct of claim 46.

According to an aspect of some embodiments of the present invention there is provided a method of identifying a putative GSK-3 substrate competitive inhibitor, the method comprising screening a plurality of substances for a substance which exhibits inhibition of at least 20% of an activity of a wild-type GSK-3 enzyme and which exhibits inhibition of no more than 20% of the activity of any of the mutated GSK-3 enzymes comprised in the polypeptide as described herein.

According to some embodiments of the invention, the screening comprises:

determining the activity of the wild-type GSK-3 enzyme in the presence and absence of each of the substances, thereby determining a level of inhibition of the activity of the wild-type GSK-3 enzyme exhibited by each of the substances;

determining the activity of the mutated GSK-3 enzyme in the presence and absence of each of the substances, thereby determining a level of inhibition of the activity of the mutated GSK-3 enzyme exhibited by each of the substances; and comparing the levels of inhibition.

According to some embodiments of the invention, the activity is phosphorylation.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

Figure 1A:
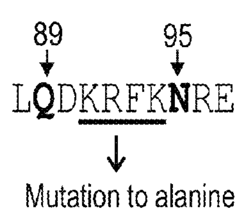
FIGS. 1A-G present the modifications made to the 88-97 binding subsite of GSK-3β (SEQ ID NO:49) which includes the 89-95 loop (SEQ ID NO:2) (FIG. 1A), Western Blot analyses showing the expression of GSK-3β mutants (FIG. 1B), a bar graph showing the phosphorylation of GSK-3 substrates by the F93A mutant (FIG. 1C); Western Blot analysis showing the expression levels of CREB and GSK-3 proteins and the phosphorylation of CREB by the F93A mutant in cells (FIG. 1D); a bar graph presenting the ratio of pCREB/
Figure 1B:
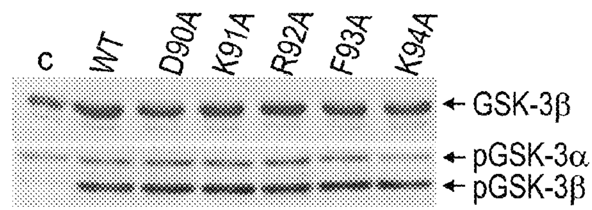
Figure 1C:
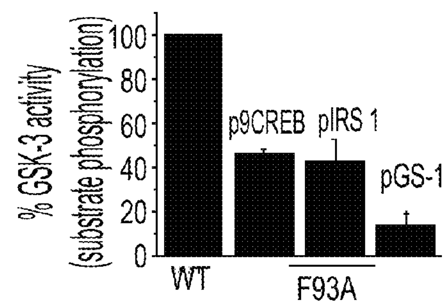
Figure 1D:
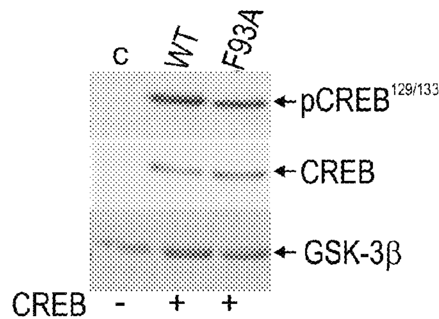
Figure 1E:
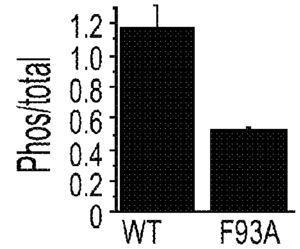
Figure 1F:
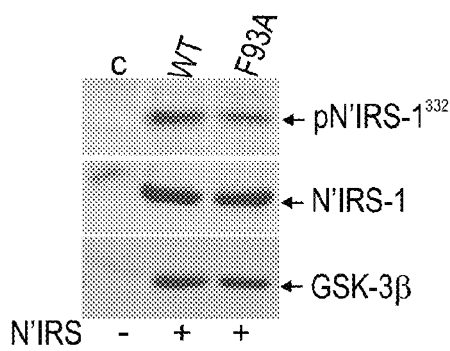
Figure 1G:
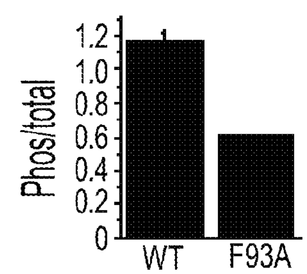
Figure 4:
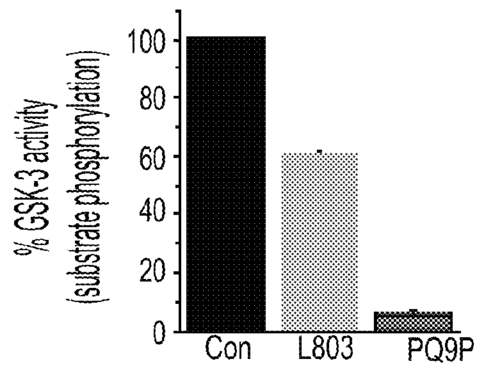
Figure 5:
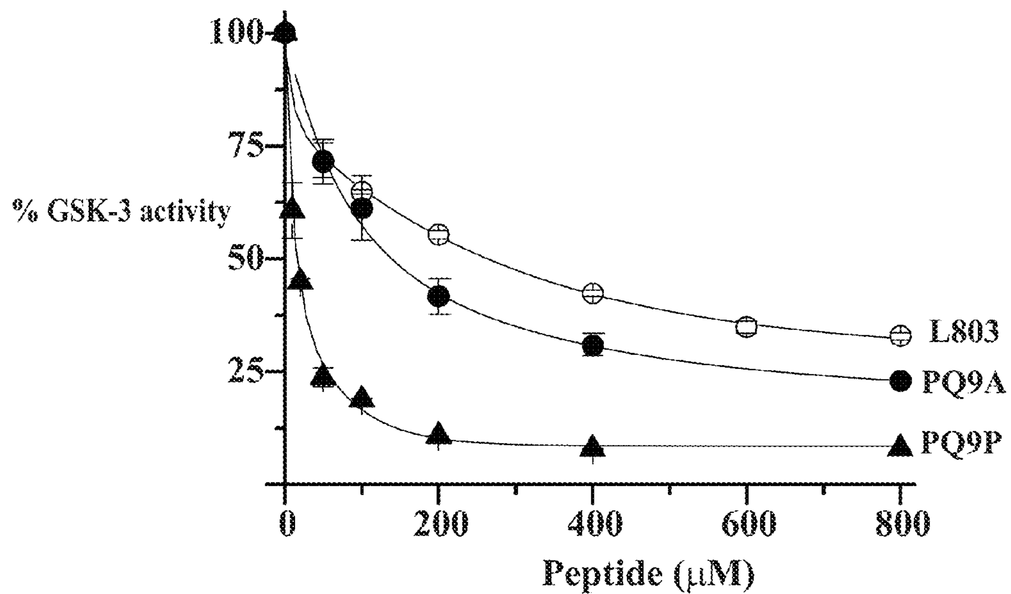
Figure 6A:
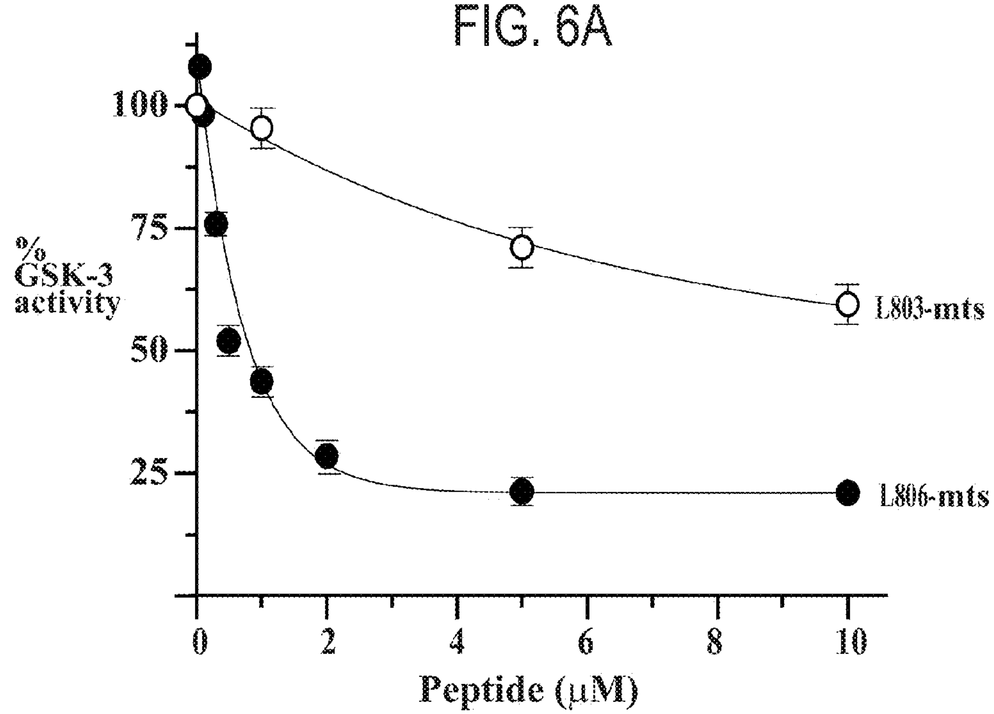
Figure 6B:
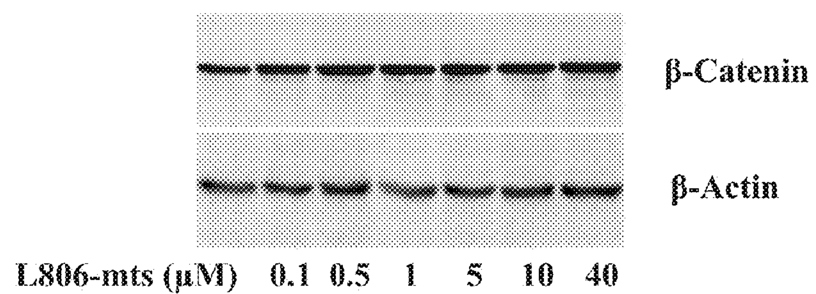
Figure 6C:
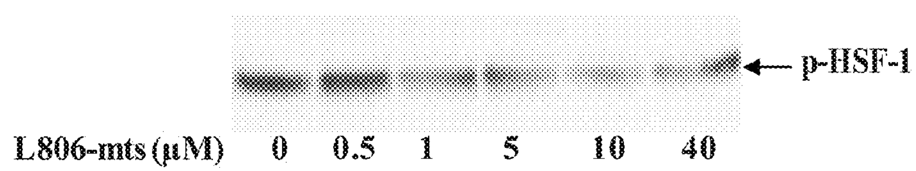
Figure 7A:
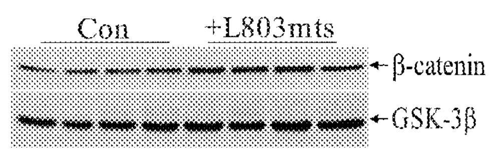
Figure 7B:
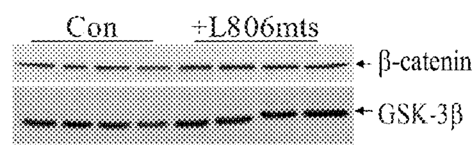

CREB in cells expressing the F93A mutant (FIG. 1E); Western Blot analysis showing the expression levels of N'IRS and GSK-3 proteins and the phosphorylation of N'IRS substrate by the F93A mutant in cells (FIG. 1F); and a bar graph presenting the ratio of PN'IRS/N'IRS in cells expressing the F93A mutant (FIG. 1G);

FIGS. 2A-C are bar graphs showing that L803-mts is a substrate competitive inhibitor of purified GSK-3β (FIG. 2A) and that both L803-mts and L803 do not inhibit substrate phosphorylation by F93A (FIGS. 2B and 2C, respectively);

FIGS. 3A-C show the exemplary L803 (SEQ ID NO:4) variants PK1A (SEQ ID NO:11), PE2A (SEQ ID NO:12), PQ9A (SEQ ID NO:13), PQ9R (SEQ ID NO:14) and PQ9Y (SEQ ID NO:15) according to some embodiments of the present invention (FIG. 3A) and the ability of these variants (250 μM each) to inhibit GSK-3β (FIGS. 3A and 3B);

FIG. 4 is a bar graph showing inhibition of GSK-3β by PQ9P (SEQ ID NO:16);

FIG. 5 presents dose-response comparative plots showing the ability of L803 (SEQ ID NO:4), PQ9A (SEQ ID NO:13) and PQ9P (SEQ ID NO:16) to inhibit GSK-3β at indicated concentrations (Substrate phosphorylation obtained in reaction with no inhibitor was defined as 100%, and results presented are means of two independent experiments each performed in duplicate±SEM);

FIGS. 6A-C present dose-response comparative plots showing the ability of L803-mts and L806-mts to inhibit GSK-3β at indicated concentrations (Substrate phosphorylation obtained in reaction with no inhibitor was defined as 100%, and results presented are means of two independent experiments each performed in duplicate±SEM) (FIG. 6A), a Western Blot analysis showing the levels of β-catenin in cells treated with L806-mts, and a Western Blot analysis showing the phosphorylation of the GSK-3 substrate HSF-1 in COS-7 cells treated with L806-mts; and FIGS. 7A-B present Western Blot analyses showing the expression level of GSK-3β and the inhibition of GSK-3, expressed as hippocampus β-catenin levels in mice treated intranasally with L803-mts (FIG. 7A) and L806-mts (FIG. 7B) and in non-treated mice (Con).

DESCRIPTION OF SPECIFIC EMBODIMENTS OF THE INVENTION

The present invention, in some embodiments thereof, relates to novel glycogen synthase kinase-3 (GSK-3) inhibitors and, more particularly, but not exclusively, to novel substrate-competitive peptide inhibitors of glycogen synthase kinase-3 (GSK-3) and to the use of such peptide inhibitors in the treatment of biological conditions associated with GSK-3 activity.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The present inventors have previously described that peptides designed after the recognition motif of a GSK-3 substrate are useful as GSK-3 substrate competitive inhibitors. See, for example, WO 01/49709 and U.S. Patent Application No. 20020147146, which are incorporated by reference as if fully set forth herein.

These peptides were designed further to the findings that GSK-3 has a unique recognition motif, and thus that short peptides which are designed with reference to this motif are highly specific GSK-3 inhibitors.

The unique recognition motif of GSK-3, as set forth in SEQ ID NO:3, is $SX_1X_2X_3S(p)$, where S is serine or threonine, each of $X_1$, $X_2$ and $X_3$ is any amino acid, and S(p) is phosphorylated serine or phosphorylated threonine. Based on this recognition motif, a set of peptides, which differ one from another in various parameters (e.g., length, phosphorylation, sequence, etc.) have been designed, synthesized and were tested for their activity as either substrates or inhibitors of GSK-3.

Based on these experiments, a number of features, which would render a peptide an efficient GSK-3 inhibitor, have been determined. For example, it was found that the phosphorylated serine or threonine residue in the motif is necessary for binding. Without this residue, the peptide will neither be a substrate nor an inhibitor. It was further determined that a serine (or threonine) residue upstream of the phosphorylated serine (or threonine) residue separated by three additional residues renders the peptide a GSK-3 substrate, whereas replacement of this serine or threonine residue by any other amino acid, preferably alanine, converts the substrate to a GSK-3 inhibitor. It was further found that the number of the additional residues, outside the recognition motif, affect the inhibition potency of the peptide, such that, for example, a total number of between 7 and 50, preferably, between 7 and 20, more preferably between 10 and 13 amino acid residues, is preferable.

Hence, it was previously described that peptides having the general amino acid sequence denoted herein as general sequence I*:

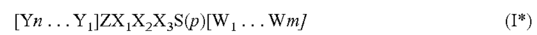

$$[Yn \ldots Y_1]ZX_1X_2X_3S(p)[W_1 \ldots Wm] \quad (I^*)$$

wherein m equals 1 or 2; n is an integer from 1 to 50; S(p) is a phosphorylated serine residue or a phosphorylated threonine residue; Z is any amino acid residue excepting serine residue or threonine residue; and $X_1$, $X_2$, $X_3$, $Y_1$-Yn and $W_1$-Wm are each independently any amino acid residue, are highly efficient and specific inhibitors of GSK-3. See, for example, U.S. Pat. Nos. 6,780,625 and 7,378,432; WO 2004/052404 and WO 2005/000192; and WO 01/49709, which are incorporated by reference as if fully set forth herein. It is noted that since these previously described inhibitors were designed so as to modify an amino acid sequence of known GSK-3 substrates, the nature of the amino acid residues presented by variables $X_1$, $X_2$, $X_3$, $Y_1$-Yn and $W_1$-Wm in the amino acid sequence I* was typically defined per the corresponding residues in the known GSK-3 substrate, namely, $X_1$, $X_2$, $X_3$ were the same as correspond amino acid residues between a serine and a phosphorylated serine in a known GSK-3 substrate, $Y_1$-Yn were the same as the amino acid residues upstream the serine residue, and $W_1$-Wm were the same as the amino acid residues downstream the phosphorylated serine or threonine residue of a known GSK-3 substrate.

It was further described that preferred peptides are those having an alanine residue at the Z position, having any amino acid residue excepting glutamic acid as $X_3$, and/or having between 7 and 20 amino acid residues, preferably between 10 and 13 amino acid residues and more preferably between 10 and 11 amino acid residues.

It was further described that a conjugate of the peptide inhibitor described above and a hydrophobic moiety, such as a fatty acid, attached at the N-terminus of the polypeptide, exerts higher inhibition of GSK-3 activity (see, for example, WO 2004/052404).

These peptides were defined as substrate competitive inhibitors.

As is well known in the art, substrate competitive enzyme inhibitors act by binding to the catalytic domain of an enzyme, thus reducing the proportion of enzyme molecules that are bound to the enzyme during the catalytic process.

While recognizing that the development of substrate competitive inhibitors depends on a molecular understanding of substrate recognition of protein kinases, efforts have been made in order to define the catalytic binding site of GSK-3. Thus, Phe67, Gln89 and Asn95 within the catalytic binding site of GSK-3β have been reported to play a role in substrates' binding [see, Ilouz et al., 2006, supra], and a cavity bordered by loop 89-QDKRFKN-95 (as set forth in SEQ ID NO:2), located in the vicinity of the GSK-3β catalytic core, has been identified as a promiscuous substrate binding subsite.

The present inventors have now further explored the role of the 89-95 loop in GSK-3β substrate binding. To this end, each of the amino acid residues within this segment was individually mutated to alanine (see, FIG. 1A). The generated mutants are denoted herein D90A, K91A, R92A, F93A, K94A, and are represented as comprising at positions 89-95 an amino acid sequence as set forth in SEQ ID NOS:6-10, respectively. These mutants were transiently expressed in HEK-293 cells. These mutants were considerably expressed, and, similarly to the wild-type (WT) GSK-3β, were phosphorylated at Tyr216 (see, FIG. 1B, lower panel), indicating that their catalytic activity was not impaired by the mutation (since phosphorylation at Tyr216 is indicative of an auto-phosphorylation process).

The generated GSK-3β mutants were tested in in vitro kinase assays with known GSK-3 substrates. The mutation at Phe93 was found to exhibit the most pronounced effect for all of tested substrates, reducing the kinase ability to phosphorylate the substrate by more than 50% (see, Table 1 hereinbelow and FIG. 1C), indicating that this position is important for substrate binding, as previously found for Phe67, Gln89 and Asn95. Phe 93 is located at the center of the 89-95 loop, it is highly exposed (81% solvent accessibility) and it faces the substrate binding subsite, facilitating contacts with a variety of residues. Further studies substantiated the findings that Phe93 interacts with GSK-3 substrates in cellular conditions (see, FIGS. 1D-1G).

The role of Phe93 and other amino acids within the 89-95 loop was tested also by determining the inhibitory activity of the previously described substrate competitive inhibitors L803 (KEAPPAPPQS(p)P; see, SEQ ID NO:4) and its cell permeable variant L803-mts (see, SEQ ID NO:5). The results indicated that both L803-mts and L803 did not inhibit the F93A mutated enzyme (see, FIGS. 3B and 3C), yet inhibited all other mutants, thus further substantiating the role of Phe93 as a most important binding position, and the role of hydrophobic interactions also within the 89-95 look as promoting inhibition of GSK-3.

These findings have led the present inventors to design novel and improved substrate competitive inhibitors, which exhibit enhanced interaction with the catalytic binding subsite of GSK-3, and thus enhanced inhibition activity. Exemplary such novel peptidic substrate competitive GSK-3 inhibitors were designed after the recognition motif of HSF, as previously described for, for example, L803, yet their hydrophobic nature was manipulated by replacing hydrophilic polar amino acids by hydrophobic amino acids residues such as alanine and proline. Various substitutions within the amino acid sequence of L803, as an exemplary substrate competitive inhibitor, have demonstrated a role for a hydrophobic amino acid residue at the first position upstream the phosphorylated serine or threonine residue, leading to a new generation of substrate competitive inhibitors of GSK-3, which exhibit improved activity.

Thus, the studies presented herein identified a role of Phe93, as well as of other amino acids within the 89-95 loop of a GSK-3 enzyme, in interacting with GSK-3 substrates and hence with GSK-3 substrate competitive inhibitors, thereby indicating that a putative substrate competitive inhibitor should exhibit an interaction with the Phe93 residue, or with an equivalent amino acid thereof, in a GSK-3 enzyme.

As used herein throughout, "GSK-3 enzyme", which is also referred to herein simply as GSK-3, describes a polypeptide having an amino acid sequence of a known GSK-3 family member (e.g., GSK-3a or GSK-3β). Unless otherwise indicated, this term refers to a wild-type GSK-3 enzyme. A GSK-3 enzyme is identified by the EC number EC 2.7.11.26. While the amino acid of GSK-3 is highly conserved, a wild-type GSK-3 can be GSK-3 of a mammal (e.g., human) or of any other organism, including microorganisms. An amino acid sequence of an exemplary GSK-3, human GSK-3β, is set forth in SEQ ID NO:1. A GSK-3 enzyme as used herein is homologous to SEQ ID NO:1 by at least 50%, at least 60%, at least 70%, at least 80%, at least 90% or can be 100% homologous.

By "wild-type" it is meant that the typical form of the enzyme as it occurs in nature, e.g., in an organism. A wild-type GSK-3 enzyme encompasses both an enzyme isolated from an organism, a chemically synthesized enzyme and a recombinantly prepared enzyme.

According to an aspect of some embodiments of the present invention there is provided a GSK-3 substrate competitive inhibitor comprising at least one moiety that is capable of interacting with at least one amino acid within the catalytic binding site of a wild-type GSK-3 enzyme, said at least one amino acid comprising a phenylalanine residue or an equivalent thereof at position 93 of said wild-type GSK-3 enzyme.

As used herein throughout, the term "position" is equivalent to the term "coordinate" with respect to an amino acid sequence.

As used herein, an equivalent amino acid refers to an amino acid which is homologous (i.e., corresponding in position in either primary or tertiary structure) and/or analogous to a specific residue or portion thereof in a given GSK-3 sequence.

An equivalent amino acid in the context of the Phe93 disclosed herein thus encompasses an analogous aromatic or otherwise hydrophobic amino acid residue at position 93 of a GSK-3 catalytic binding, as well as a phenylalanine residue or an analogous amino acid residue thereof which is located at a position that corresponds, either in primary or tertiary structure, to position 93 of, for example, GSK-3β enzyme as set forth herein in SEQ ID NO:1.

By analogous it is meant, for example, a natural amino acid that resembles in chemical nature to the amino acid residue (e.g., Phe and Tyr are analogous; Asn and Gln are analogous; Leu and Ile are analogous), or a non-natural amino acid that resembles in chemical nature to the amino acid residue.

It has been shown most species exhibit a GSK-3 sequence with a conserved amino acid sequence of the 89-95 loop, and thus feature Phe at position 93, while some unicellular species exhibit a GSK-3 sequence in which a Tyr residue or an Ile residue are at position 93. This indicates a general role for hydrophobic interactions with position 93 of a GSK-3, in almost all species where GSK-3 is expressed.

By "moiety" it is meant a chemical group, either per se or which forms a part of e.g., a chemical compound, an amino acid, peptide or polypeptide.

By "interacting" it is meant a chemical interaction as a result of, for example, hydrophobic interactions, including aromatic interactions, electrostatic interactions, Van der Waals interactions and hydrogen bonding.

Since phenylalanine comprises a hydrophobic aromatic side chain (phenyl), in some embodiments, the interaction of the inhibitor with the bonding site of GSK-3 comprises hydrophobic interactions.

As used herein, the expressions "phenylalanine at position 93", F93, Phe93, Phe 93, are all used interchangeably to denote the type of the 93$^{rd}$ amino acid residue within an amino acid sequence of GSK-3, when numbered downstream of its N-terminus, or of an equivalent amino acid thereof, as defined herein.

Thus, in some embodiments, the moiety that is capable of interacting with Phe93 in GSK-3, is capable of exhibiting hydrophobic interactions with the aromatic side chain of Phe93.

Representative examples of such moieties include, but are not limited to, hydrocarbons, including alkyls, preferably of 2 or more carbon atoms, cycloalkyls, aryls, each can optionally be substituted, heteroalicyclic moieties, and heteroaryl moieties, as these are defined herein.

In some embodiments, the moiety is a rigid moiety, namely, is characterized by a low number of free rotations. Exemplary rigid moieties include, but are not limited to, cyclic moieties, such as cycloalkyl, heteroalicyclic, aryl or heteroaryl, with aromatic cyclic moieties, aryls and heteroaryls being more rigid then others and hence preferred.

Thus, in some embodiments, the moiety is an aryl or heteroaryl, and the inhibitor is a substance that comprises an aryl or heteroaryl, as defined herein. Such moieties further account for possible aromatic interactions with Phe93.

In some embodiments, the inhibitor comprises two or more moieties that are capable of interacting with Phe93 and optionally also with other amino acid residues within the catalytic binding site of GSK-3.

Thus, in some embodiments, the inhibitor as described herein is such that is capable of interacting both with Phe93 of GSK-3 and with one or more additional amino acid residues within the catalytic binding site of a GSK-3 enzyme.

Any of the hitherto identified amino acid residues within the catalytic binding site of GSK-3 are contemplated, including, but not limited to, those described in Ilouz et al. (2006, supra), in Dajani et al. (supra) and in and in WO 2005/000192.

Thus, in addition to comprising a moiety that is capable of interacting with Phe93, an inhibitor as disclosed herein further comprises moieties that are capable of interacting with one or more of such additional amino acid moieties. It is preferred that the moiety that is capable of interacting with Phe93 and the one or more additional moieties that are capable of interacting with other positions within the GSK-3 catalytic domain would be in a suitable proximity and orientation so as to allow mutual interactions with the different subsites within the catalytic binding site.

In some embodiments, an inhibitor as described herein is such that is capable of interacting, in addition to the Phe93, with the phosphate binding pocket of GSK-3, namely, with one or more Arg86, Arg196 and Lys205.

In some embodiments, an inhibitor as described herein is such that is capable of interacting, in addition to Phe93, with a hydrophobic patch that is defined by Val214, I216 and Y216.

In some embodiments, the inhibitor as described herein is such that is capable of interacting both with Phe93 of GSK-3 and with one or more of the additional amino acids Phe67, Gln89, Asp90, Lys91, Arg92, Lys94 and Asp95 in the GSK-3 enzyme, or with one or more of Phe67, Gln89, Asp90, Arg92, Lys 94 and Asp95 in the GSK-3 enzyme, or with one or more of Phe67, Gln89 and Asn95.

Thus, in some embodiments, a GSK-3 inhibitor as described herein comprises one or more moieties that are capable of interacting with Phe93 (e.g., hydrophobic moieties), and one or more moieties that are capable of interacting with Phe67 (e.g., hydrophobic moieties). In these embodiments, the hydrophobic moieties are preferably spaced within the inhibitor in a configuration (proximity and orientation) that allows interactions with both amino acids.

In some embodiments, a GSK-3 inhibitor as described herein comprises one or more moieties that are capable of interacting with Phe93 (e.g., hydrophobic moieties), and one or more moieties that are capable of interacting with Gln89 (e.g., via hydrogen bonding with its amide). In these embodiments, the moieties are preferably spaced within the inhibitor in a configuration (proximity and orientation) that allows interactions with both amino acids.

In some embodiments, a GSK-3 inhibitor as described herein comprises one or more moieties that are capable of interacting with Phe93 (e.g., hydrophobic moieties), and one or more moieties that are capable of interacting with Asn95 (e.g., via hydrogen bonding with its amide). In these embodiments, the moieties are preferably spaced within the inhibitor in a configuration (proximity and orientation) that allows interactions with both amino acids.

In some embodiments, a GSK-3 inhibitor as described herein comprises one or more moieties that are capable of interacting with Phe93 (e.g., hydrophobic moieties), and one or more moieties that are capable of interacting with Asn95 and Gln89 (e.g., via hydrogen bonding with their amide). In these embodiments, the moieties are preferably spaced within the inhibitor in a configuration (proximity and orientation) that allows interactions with these amino acids.

In some embodiments, a GSK-3 inhibitor as described herein comprises one or more moieties that are capable of interacting with Phe93 (e.g., hydrophobic moieties), and one or more moieties that are capable of interacting with one or both Gln89 and Asn95 (e.g., via hydrogen bonding with its amide) and with Phe67 (via hydrophobic interactions). In these embodiments, the moieties are preferably spaced within the inhibitor in a configuration (proximity and orientation) that allows interactions with these amino acids.

In some embodiments, a GSK-3 inhibitor as described herein comprises one or more moieties that are capable of interacting with Phe93 (e.g., hydrophobic moieties), and one or more moieties that are capable of interacting with one or more of Arg86, Arg196 and Lys205 (e.g., via hydrogen bonding with the amine). In these embodiments, the moieties are preferably spaced within the inhibitor in a configuration (proximity and orientation) that allows interactions with these amino acids.

In some embodiments, a GSK-3 inhibitor as described herein comprises one or more moieties that are capable of interacting with Phe93 (e.g., hydrophobic moieties), and one or more moieties that are capable of interacting with one or more of the amino acids of a hydrophobic patch within the GSK-3 catalytic binding site as described herein (e.g., via hydrophobic interactions). In these embodiments, the moieties are preferably spaced within the inhibitor in a configuration (proximity and orientation) that allows interactions with these amino acids.

Any combination of moieties that are suitably spaced in a configuration that allows interactions with any combination of the amino acids described herein are also contemplated for an inhibitor as described herein.

Determining is a substance or a moiety is capable of interacting with Phe93 or an equivalent amino acid thereof can be performed by methods known in the art, as is further detailed hereinbelow. In some embodiments, computational modeling can be used to evaluate the interaction of a substance with Phe93. In some embodiments, the activity of a wild-type GSK-3 and the activity of a corresponding mutated GSK-3, in which Phe93 is substituted by another amino acid (e.g., alanine), is determined in the presence of the inhibitor. Reduction of the inhibition activity of the substance when tested with the mutated GSK-3, compared to its inhibition activity of the wild-type GSK-3, is indicative of an interaction of the inhibitor with Phe93.

The substrate competitive inhibitor disclosed herein can be a small molecule, namely a non-peptidic organic compound. Exemplary compounds include compounds possessing one or more of the hydrophobic moieties as described herein (e.g., aryl or heteroaryl moieties) and optionally one or more moieties that are capable of interacting with one or more of the additional amino acid residues within the catalytic bonding site, as described herein.

In some embodiments, the substrate competitive inhibitor is a peptide (or a polypeptide).

In some embodiments, the peptide comprises one or more of a hydrophobic amino acid residue, as defined herein, which are suitably positioned with respect to other functional amino acid moieties so as to allow interactions with other subsites within the catalytic binding site of GSK-3 (e.g., the phosphate binding pocket).

In some embodiments, the peptide is based on a recognition motif of a GSK-3 substrate as defined herein and was previously described (see, for example, WO 01/49709).

Excluded from the scope of these embodiments of the present invention are substances, including small molecules and peptides already reported in the art as acting as GSK-3 inhibitors. These include, for example, substrate competitive inhibitors of GSK-3 inhibitors as described in Plotkin et al. (2003) *J. Pharmacol. Exp. Ther.*, 974-980], in Kaidanovich-Beilin & Eldar-Finkelman (2005) *J. Pharmacol. Exp. Ther.* 316:17-24; in Rao et al. (2007) *Diabetologia* 50, 452-60; Kim et al. (2006) *Neuron* 52, 981-96; in Chen et al. (2004) *Faseb J* 18, 1162-4; in Kaidanovich-Beilin et al. (2004) *Biol. Psychiatry* 55:781-4; in Shapira et al. (2007) *Mol. Cell Neurosci.* 34, 571-7]; in Ilouz et al. (2006) *J. Biol. Chem.* 281, 30621-30]; in U.S. Pat. Nos. 6,780,625 and 7,378,432; in WO 2004/052404, WO 2005/000192; and WO 01/49709; in Liberman, Z. & Eldar-Finkelman, H. (2005) *J. Biol. Chem.* 280, 4422-8; in Liberman et al. (2008) *Am. J. Physiol. Endocrinol. Metab.* 294, E1169-77; and in Bertrand et al. (2003) *J. Mol. Biol.* 333, 393-407.

As discussed hereinabove, the present inventors have designed novel peptides, which are based on the a recognition motif of a GSK-3 substrate, and are further designed to feature defined characteristics which provide for increased interaction of the peptide with the catalytic binding site of GSK-3, and particularly with Phe93 (or an equivalent amino acid residue, as defined herein).

Thus, newly designed peptides are disclosed herein. These peptides are collectively represented by the amino acid sequence I as follows:

$$[Yn \ldots Y_1]ZX_1X_2X_3S(p)[W_1 \ldots Wm] \quad (I)$$

wherein, m equals 1 or 2;

n is an integer from 3 to 7, such that said polypeptide consists of 10 to 13 amino acid residues;

S(p) is a phosphorylated serine residue or a phosphorylated threonine residue;

Z is any amino acid residue excepting serine residue or threonine residue;

$X_1$, $X_2$, $Y_1$-Yn and $W_1$-Wm are each independently any amino acid residue; and $X_3$ is a hydrophobic amino acid residue.

According to some embodiments of the present invention, the peptides described herein can be considered as sequenced based on a natural or otherwise identified GSK-3 substrate (e.g., CREB or HSF-1), while maintaining the identified recognition motif of GSK-3 described hereinabove (see, SEQ ID NO:3), which includes phosphorylated serine or threonine residue, and while replacing the serine or threonine that is at the fourth position upstream of the phosphorylated serine or threonine.

The phrase "natural GSK-3 substrate" or "known GSK-3 substrate" describes any peptide (or protein) which is known to be phosphorylated by GSK-3 in a biological system. By "biological system" it is meant a system of any living species including, for example, vertebrates, poultry, mammals, human beings and microorganisms, including unicellular organisms. Representative examples of natural GSK-3 substrates include, but are not limited to, HSF-1, pIRS-1, p9CREB, pGS-1, phosphorylated peptides derived from the insulin receptor substrate-1 (IRS-1) [see, for example, Liberman and Eldar-Finkelman (2005) supra], cAMP responsive element binding protein (CREB), and glycogen synthase, some of which are set forth herein as having SEQ ID NOS: 18-20.

It is expected that during the life of a patent maturing from this application additional relevant GSK-substrates will be identified and the scope of the term "natural GSK-3 substrate" is intended to include all such new substrates a priori.

As discussed hereinabove, in the peptides described herein, the amino acid residue at the first position upstream of the phosphorylated serine or threonine (denoted as $X_3$) is a hydrophobic amino acid residue.

Thus, in some embodiments, the peptides described herein can be considered as sequenced based on a natural or otherwise identified GSK-3 substrate, while maintaining the identified recognition motif of GSK-3 described hereinabove (see, SEQ ID NO:3), which includes phosphorylated serine or threonine residue, and while replacing the serine or threonine residue that is at the fourth position upstream of the phosphorylated serine or threonine by any other amino acid residue and while replacing the amino acid residue at the first position upstream of the phosphorylated serine or threonine by a hydrophobic amino acid residue.

The term "hydrophobic", as used herein with reference to an amino acid or any other substance or moiety, describes a feature of the substance that renders its solubility in water lower than its solubility in hydrophobic organic solvents.

The term "hydrophobic" thus often translates into values such as Log P, which describes the partition coefficient of a substance between an aqueous phase (water) and an oily phase (1-octanol).

According to some embodiments of the present invention, a hydrophobic amino acid has a Log P value that is higher (i.e., less negative) than −3, or higher than −2.9, or higher than −2.8, or higher than −2.7, or higher than −2.6, or even higher than −2.5.

Exemplary hydrophobic amino acids include, but are not limited to, glycine, alanine, leucine, isoleucine, valine, proline, phenylalanine, methionine, cysteine and tryptophan.

In some embodiments, $X_3$ is a proline residue or an alanine residue.

In some embodiments, $X_3$ is a proline residue.

In some embodiments, $X_3$ is an amino acid that an a hydrophobic side chain which is rigid, thus ensuring better interaction (reduced entropy) with the catalytic binding site. Exemplary such amino acids have a side chain that comprises an aryl (e.g., tryptophan and phenylalanine) or a heteroaryl (e.g., proline).

$X_1$ and $X_2$ in the amino acid sequence of the peptide described herein can be any amino acid, as described herein.

In some embodiments, at least one, or both, of $X_1$ and $X_2$ is a hydrophobic amino acid, as described herein.

Thus, in some embodiments, each of $X_1$, $X_2$ and $X_3$ is a hydrophobic amino acid residue, as described herein (e.g., alanine or proline).

In some embodiments, $X_1$ and $X_2$ are each a proline residue.

In some embodiments, each of $X_1$, $X_2$ and $X_3$ is a proline residue.

In some embodiments, S(p) is a phosphorylated serine residue.

The amino acid denoted Z in the amino acid sequence of the peptide described herein can be any amino acid, as described herein.

In some embodiments, Z is an alanine residue.

In some embodiments, a peptide as described herein comprises any one of the following amino acid sequences as the moiety denoted as $ZX_1X_2X_3S(p)$ in amino acid sequence I, as non-limiting examples:

Ala-Pro-Pro-Pro-phosphorylated serine (SEQ ID NO:21)

Ala-Pro-Pro-Pro-phosphorylated threonine (SEQ ID NO:22)

Ala-Ala-Pro-Pro-phosphorylated serine (SEQ ID NO:23)

Ala-Ala-Pro-Pro-phosphorylated threonine (SEQ ID NO:24)

Ala-Ala-Ala-Pro-phosphorylated serine (SEQ ID NO:25)

Ala-Ala-Ala-Pro-phosphorylated threonine (SEQ ID NO:26)

Ala-Pro-Ala-Pro-phosphorylated serine (SEQ ID NO:27)

Ala-Pro-Ala-Pro-phosphorylated threonine (SEQ ID NO:28)

Ala-Gly-Pro-Pro-phosphorylated serine (SEQ ID NO:29)

Ala-Gly-Pro-Pro-phosphorylated threonine (SEQ ID NO:30)

Ala-Gly-Gly-Pro-phosphorylated serine (SEQ ID NO:31)

Ala-Gly-Gly-Pro-phosphorylated threonine (SEQ ID NO:32)

Ala-Pro-Gly-Pro-phosphorylated serine (SEQ ID NO:33)

Ala-Pro-Gly-Pro-phosphorylated threonine (SEQ ID NO:34)

Ala-Leu/Ile-Pro-Pro-phosphorylated serine (SEQ ID NO:35)

Ala-Leu/Ile-Pro-Pro-phosphorylated threonine (SEQ ID NO:36)

Ala-Leu/Ile-Leu/Ile-Pro-phosphorylated serine (SEQ ID NO:37)

Ala-Leu/Ile-Leu/Ile-Pro-phosphorylated threonine (SEQ ID NO:38)

Ala-Pro-Leu/Ile-Pro-phosphorylated serine (SEQ ID NO:39)

Ala-Pro-Leu/Ile-Pro-phosphorylated threonine (SEQ ID NO:40)

Ala-Val-Pro-Pro-phosphorylated serine (SEQ ID NO:41)

Ala-Val-Pro-Pro-phosphorylated threonine (SEQ ID NO:42)

Ala-Val-Val-Pro-phosphorylated serine (SEQ ID NO:43)

Ala-Val-Val-Pro-phosphorylated threonine (SEQ ID NO:44)

Ala-Pro-Val-Pro-phosphorylated serine (SEQ ID NO:45)

Ala-Pro-Val-Pro-phosphorylated threonine (SEQ ID NO:46).

In some embodiments, in any of these moieties, the Pro residue at the first position upstream the phosphorylated serine or threonine ($X_3$) is replaced by any of the other hydrophobic moieties as described herein (e.g., Phe or Trp).

It is to be noted that for $X_1$, $X_2$ and $X_3$, any combination of 3 hydrophobic amino acid residues as defined herein is contemplated in some embodiments of the present invention, and that any such combination can be combined with either a phosphorylated serine residue or a phsophorylated threonine residue at the position denoted S(p), and with any amino acid residue at the position denoted Z.

In some embodiments, the number and nature of amino acid residues downstream the residue denoted as S(p) and upstream the residue denoted as Z, is determined by the amino acid sequence of the GSK-3 substrate after which the peptide is designed.

In some embodiments, m is 1.

In some embodiments, $W_1$ is a proline residue, although any other amino acid residue at this position, and at position $W_2$ (if present, when m=2) is also contemplated.

In some embodiments, n is 5, such that the peptide comprises an amino acid sequence as described herein, in which upstream to Z there are amino acid residues denoted as $Y_1$-$Y_5$.

In some embodiments, when the peptide is designed after the substrate HSF-1, $Y_1$-$Y_5$ has the amino acid sequence Lys-Glu-Ala-Pro-Pro, as set forth in any of SEQ ID NOS:11-16. However, any other sequence of amino acid residues can be included within the amino acid residues upstream to Z.

In other embodiments, $Y_3$-$Y_5$ are each a hydrophobic amino acid residue (as defined herein, e.g., proline and/or alanine), and at least one of $Y_1$ and $Y_2$ is a hydrophobic amino acid residue (as defined herein, e.g., proline or alanine).

Exemplary peptides are those having the following amino acid sequences:

Lys-Glu-Ala-Pro-Pro-Ala-Pro-Pro-Pro-phosphorylated Ser-Pro (PQ9P; SEQ ID NO:16);

Lys-Glu-Ala-Pro-Pro-Ala-Pro-Pro-Ala-phosphorylated Ser-Pro (PQ9A; SEQ ID NO:13);

Ala-Glu-Ala-Pro-Pro-Ala-Pro-Pro-Gln-phosphorylated Ser-Pro (PK1A; SEQ ID NO:11);

Lys-Ala-Ala-Pro-Pro-Ala-Pro-Pro-Gln-phosphorylated Ser-Pro (PE2A; SEQ ID NO:12).

In some embodiments, the polypeptide has the amino acid sequence: Lys-Glu-Ala-Pro-Pro-Ala-Pro-Pro-Pro-phosphorylated Ser-Pro (PQ9P; SEQ ID NO:16).

In addition to the inclusion of hydrophobic amino acid residues within the amino acid sequence of the peptide described herein, as presented herein, any of the peptides described herein can further comprise a hydrophobic moiety covalently attached thereto.

As used herein the phrase "hydrophobic moiety" refers to any substance that is characterized by hydrophobicity, namely, its solubility in water is much lower than its solubility in hydrophobic organic solvents, as defined herein.

In some embodiments, any hydrophobic moiety that is structurally suitable for interacting with a hydrophobic patch within a GSK-3 dimer, can be attached to the polypeptide described above.

The hydrophobic patch has been previously described by Dajani et al. (2001, supra). The crystallization data of Dajani et al. showed that GSK-3 is crystallized as a dimer, suggesting that this dimerization has biological relevance. The catalytic region (residues 216-220) of one monomer (a) appears to interact with the N-terminus of an α-helix (residues 262-273) of the other monomer (b). This interaction of the two monomers (a) and (b) forms a hydrophobic patch in monomer (b).

Alternatively, or in addition, the hydrophobic moiety is selected such that it enhances cell permeability of the peptide. Enhanced cell permeability can be determined by any method known in the art, for example, by determining a cellular uptake in in vitro studies.

Representative examples of hydrophobic substances from which the hydrophobic moiety of the present invention can be derived include, without limitation, substituted and unsubstituted, saturated and unsaturated hydrocarbons, where the hydrocarbon can be an aliphatic, an alicyclic or an aromatic compound and preferably includes at least 4 carbon atoms, more preferably at least 8 carbon atoms, more preferably at least 10 carbon atoms. In some embodiments, the hydrocarbon bears a functional group which enables its attachment to an amino acid residue. Representative examples of such a functional group include, without limitation, a free carboxylic acid (C(═O)OH), a free amino group ($NH_2$), an ester group (C(═O)OR, where R is alkyl, cycloalkyl or aryl), an acyl halide group (C(═O)A, where A is fluoride, chloride, bromide or iodide), a halide (fluoride, chloride, bromide or iodide), a hydroxyl group (OH), a thiol group (SH), a nitrile group (C≡N), a free C-carbamic group (NR"—C(═O)—OR', where each of R' and R" is independently hydrogen, alkyl, cycloalkyl or aryl), a free N-carbamic group (OC(═O)—NR'—, where R' is as defined above), a thionyl group ($S(=O)_2A$, where A is halide as defined above) and the like.

In some embodiments, the hydrophobic moiety comprises one or more fatty acid(s).

Representative examples of fatty acids that are usable in the context of the present invention include, without limitation, saturated or unsaturated fatty acids that have more than 10 carbon atoms, preferably between 12 and 24 carbon atoms, such as, but not limited to, myristic acid, lauric acid, palmitic acid, stearic acid, oleic acid, linoleic acid, linolenic acid, arachidonic etc., with myristic acid being presently the most preferred.

The hydrophobic moiety according to some embodiments of the present invention can be a fatty acid, or derived from any other hydrophobic substance as described above, per se, such that the fatty acid, or any other hydrophobic substance, is covalently attached directly to an amino acid residue of the peptide (via, for example, en ester bond or an amide bond). Alternatively, the hydrophobic moiety can be an amino acid residue that is modified to include a fatty acid, or any other hydrophobic substance as described hereinabove, such that this modified amino acid residue is attached to the peptide via a peptide bond or a substituted peptide bond, as is described herein. Further alternatively, the hydrophobic moiety can be a short peptide in which one or more amino acid residues are modified to include a fatty acid or any other hydrophobic substance as described herein. Such a peptide preferably includes between 2 and 15 amino acid residues and is attached to the peptide via a peptide bond or a substituted peptide bond, as is described herein.

As an alternative to, or in combination with the hydrophobic moiety described above, the hydrophobic moiety, according to the present invention, can comprise a hydrophobic peptide sequence. The hydrophobic peptide sequence, according to the present invention, preferably includes between 2 and 15 amino acid residues, more preferably between 2 and 10 amino acid residues, more preferably between 2 and 5 amino acid residues, in which at least five consecutive amino acid residues are hydrophobic amino acid residues.

Alternatively, the hydrophobic amino acid residue can include any other amino acid residue, which has been modified by incorporation of a hydrophobic moiety thereto.

The hydrophobic moiety or moieties of the present invention are preferably attached to one or more termini of the peptide, namely the N-terminus and/or the C-terminus of the polypeptide. In some embodiments, the hydrophobic moiety is attached, directly or indirectly, as described herein, to the N-terminus of the polypeptide.

An exemplary peptide has the amino acid sequence Myristic-Gly-Lys-Glu-Ala-Pro-Pro-Ala-Pro-Pro-Pro-phosphorylated Ser-Pro (PQ9P; SEQ ID NO:17).

Additional exemplary peptides are those represented by any of SEQ ID NOS:11-13, and/or those comprising any of SEQ ID NOS:21-46, as described herein, which have a hydrophobic moiety attached thereto, as described herein. Any combination of such peptides and a hydrophobic moiety as described herein (e.g., a fatty acid as described herein and/or an amino acid substituted by a fatty acid as described herein and/or a hydrophobic amino acid sequence as described herein) is contemplated.

Further according to embodiments of the present invention, there is provided a process of preparing the peptides described herein.

In one embodiment, the peptide of the present invention is prepared by a chemical synthesis, using well known chemical procedures, such as solution or solid-phase peptide synthesis, or semi-synthesis in solution. The peptide can be chemically synthesized, for example, by the solid phase peptide synthesis of Merrifield et al (1964). Alternatively, a peptide can be synthesized using standard solution methods (see, for example, Bodanszky, 1984). Newly synthesized peptides can be purified, for example, by high performance liquid chromatography (HPLC), and can be characterized using, for example, mass spectrometry or amino acid sequence analysis.

Alternatively, the peptides of the invention can be provided recombinantly. Systems for cloning and expressing the peptide include various microorganisms and cells that are well known in recombinant technology. These include, for example, various strains of *E. coli, Bacillus, Streptomyces*, and *Saccharomyces*, as well as mammalian, yeast and insect cells. The peptide can be produced as a peptide or fusion protein (e.g., tagged peptide). Suitable vectors for producing the peptide are known and available from private and public laboratories and depositories and from commercial vendors. See Sambrook et al, (1989). Recipient cells capable of expressing the gene product are then transfected. The transfected recipient cells are cultured under conditions that permit expression of the recombinant gene products, which are recovered from the culture. Host mammalian cells, such as Chinese Hamster ovary cells (CHO) or COS-1 cells, can be used. These hosts can be used in connection with poxvirus vectors, such as vaccinia or swinepox. Suitable non-pathogenic viruses that can be engineered to carry the synthetic gene into the cells of the host include poxviruses, such as vaccinia, adenovirus, retroviruses and the like. A number of such non-pathogenic viruses are commonly used for human gene therapy, and as carrier for other vaccine agents, and are known and selectable by one of skill in the art. The selection of other suitable host cells and methods for transformation, culture, amplification, screening and product production and purification can be performed by one of skill in the art by reference to known techniques (see, e.g., Gething et al, 1981).

Once the peptide is provided, a hydrophobic moiety or moieties can be conjugated thereto, if desired, by commonly used techniques. For example, in cases where the hydrophobic moiety is a fatty acid, techniques for adding a fatty acid (e.g., myristic acid) to an amino acid residue within the peptide sequence are used. Alternatively, an amino acid residue is modified to include a hydrophobic moiety such as fatty acid and is thereafter attached to the peptide by known chemical procedures, as is described hereinabove.

In cases where the hydrophobic moiety comprises a hydrophobic peptide sequence, the hydrophobic peptide can be prepared using the methods described hereinabove and thereafter be conjugated to the polypeptide. Alternatively, the conjugate can be prepared recombinantly, using systems, as described hereinabove, for cloning and expressing a fused polypeptide that comprises the peptide as described herein and such a hydrophobic peptide sequence.

As is demonstrated in the Examples section that follows, exemplary peptides according to some embodiments of the present invention exhibit high inhibitory effect toward GSK-3.

As is discussed hereinabove, these peptides are characterized by specificity towards GSK-3, a specificity which is derived from the unique recognition motif of GSK-3, which, unlike other kinases, includes a phosphorylated serine or threonine residue, and the fact that the sequence of the peptide portion thereof is based on this recognition motif.

The additional manipulation made to the GSK-3 recognition motif while designing the peptides disclosed herein render these peptides efficient substrate competitive inhibitors of GSK-3, and thus more specific as compared with other protein kinase inhibitors that are typically ATP competitive compounds and thus non-specific.

Thus, the high inhibitory activity of the peptides disclosed herein is derived from both, the replacement of the phosphorylated residue at the Z position by a non-phosphorylated residue, which renders the enzyme inactive in phosphorylation, and the incorporation of a hydrophobic amino acid residue at the indicated position within the recognition motif, which provides for enhanced interaction with a subunit of the enzyme's catalytic binding site, as discussed herein.

Hence, according to another aspect of some embodiments of the present invention, there is provided a method of inhibiting an activity of GSK-3, which is effected by contacting cells expressing GSK-3 with an effective amount of any of the peptides described herein (e.g., represented by amino acid sequence I), or by any of the GSK-3 substrate competitive inhibitors as described herein (which are capable of interacting with Phe93 or an equivalent thereof).

As used herein, the term "effective amount" is the amount determined by such considerations as are known in the art, which is sufficient to reduce the activity of GSK-3 by at least 5%, at least 10%, at least 20%, at least 50% and even at least 80%, 90% or by 100%. Typical assays for measuring kinase activity can be used for determining the inhibitory activity of the peptides as described herein.

As is demonstrated in the Examples section that follows, a representative example of a peptide according to some embodiments of the present invention strongly inhibits GSK-3, with an $IC_{50}$ value of less than 50 μM, and even less than 1 μM, as measured by in vitro kinase assay.

Hence, the effective amount of a peptide as described herein can range from about 0.1 micromolar to about 100 micromolar, or from about 0.1 micromolar and about 50 micromolar, or from about 0.1 micromolar to about 20 micromolar, or from about 1 micromolar to about 20 micromolar, including any intermediate value between the indicated ranges.

As used herein throughout the term "about" refers to ±10%.

As is further demonstrated in the Examples section that follows, the inhibition activity of the peptides described herein was tested in both in vitro and in vivo assays. Thus, the method according to this aspect of the present invention can be effected by contacting the cells with the described peptides in vitro, ex vivo and in vivo.

Cells expressing GSK-3 can be derived from any biological sample, including, but not limited to, cell cultures or extracts thereof, enzyme preparations suitable for in vitro assays, biopsied material obtained from a mammal or extracts thereof, and samples of blood, saliva, urine, feces, semen, tears, spinal fluid, and any other fluids or extracts thereof.

In some embodiments, the method according to these embodiments, utilizes the peptides as described herein as active agents in biological assays, and in particular, as GSK-3 (substrate competitive) inhibitors in such assays.

As the peptides described herein do not include the required phosphorylated residue (at the Z position), GSK-3, while being bound thereto, is rendered inactive in phosphorylation reactions. Thus, the method according to these embodiments of the present invention preferably pertains to inhibition of the phosphorylation and/or autophosphorylation activity of GSK-3. In some embodiments, the activity is phosphorylation activity.

The method according to these embodiments of the present invention can be further effected by contacting the cells with an additional active ingredient that is capable of altering an activity of GSK-3, as is detailed hereinbelow.

The inhibition of GSK-3 activity is a way to increase insulin activity in vivo. High activity of GSK-3 impairs insulin action in intact cells. This impairment results from the phosphorylation of insulin receptor substrate-1 (IRS-1) serine residues by GSK-3. Studies performed in patients with type II diabetes (non-insulin dependent diabetes mellitus, NIDDM) show that glycogen synthase activity is markedly decreased in these patients, and that decreased activation of protein kinase B (PKB), an upstream regulator of GSK-3, by insulin is also detected. Mice susceptible to high fat diet-induced diabetes and obesity have significantly increased GSK-3 activity in epididymal fat tissue. Increased GSK-3 activity expressed in cells resulted in suppression of glycogen synthase activity.

Inhibition of GSK-3 activity therefore provides a useful method for increasing insulin activity in insulin-dependent conditions. For example, treatment with the peptides as described herein can result in improved glucose uptake and/or glucose tolerance.

Thus, according to another aspect of the present invention there is provided a method of potentiating insulin signaling, which is effected by contacting insulin responsive cells with an effective amount, as is defined hereinabove, of the peptide as described herein.

Contacting can be effected in vitro, as described herein, for example, by contacting a biological sample as described herein with one or more of the peptides described herein, or ex vivo, or in vivo, by administering a peptide as described herein to a patient in need thereof.

As used herein, the phrase "potentiating insulin signaling" includes an increase in the phosphorylation of insulin receptor downstream components and an increase in the rate of glucose uptake as compared with glucose uptake in untreated subjects or cells.

Potentiation of insulin signaling, in vivo, resulting from administration of the peptides as described herein, can be monitored as a clinical endpoint. In principle, the easiest way to look at insulin potentiation in a patient is to perform the glucose tolerance test. After fasting, glucose is given to a patient and the rate of the disappearance of glucose from blood circulation (namely glucose uptake by cells) is measured by assays well known in the art. Slow rate (as compared to healthy subject) of glucose clearance will indicate insulin resistance. The administration of a GSK-3 inhibitor such as the peptides described herein to an insulin-resistant patient increases the rate of glucose uptake as compared with a non-treated patient. The peptide may be administered to the patient for a longer period of time, and the levels of insulin, glucose, and leptin in blood circulation (which are usually high) may be determined. Decrease in glucose levels will indicate that the peptide potentiated insulin action. A decrease in insulin and leptin levels alone may not necessarily indicate potentiation of insulin action, but rather will indicate improvement of the disease condition by other mechanisms.

By inhibiting GSK-3 activity and/or potentiating insulin signaling, the peptides described herein may be effectively utilized for treating any biological condition that is associated with GSK-3.

Hence, according to another aspect of some embodiments of the present invention, there is provided a method of treating a biological condition associated with GSK-3 activity. The method, according to this aspect of the present invention, is effected by administering to a subject in need thereof a therapeutically effective amount of the peptide as described herein.

The phrase "biological condition associated with GSK-3 activity" as used herein includes any biological or medical condition or disorder in which effective GSK-3 activity is identified, whether at normal or abnormal levels. The condition or disorder may be caused by the GSK-3 activity or may simply be characterized by GSK-3 activity. That the condition is associated with GSK-3 activity means that some aspects of the condition can be traced to the GSK-3 activity. Such a biological condition can also be regarded as a biological or medical condition mediated by GSK-3.

Herein, the term "treating" includes abrogating, substantially inhibiting, slowing or reversing the progression of a condition or disorder, substantially ameliorating clinical symptoms of a condition or disorder or substantially preventing the appearance of clinical symptoms of a condition or disorder. These effects may be manifested, for non-limiting examples, by a decrease in the rate of glucose uptake with respect to type II diabetes or by halting neuronal cell death with respect to neurodegenerative disorders, as is detailed hereinbelow.

The term "administering" as used herein describes a method for bringing a peptide as described herein and cells affected by the condition or disorder together in such a manner that the peptide can affect the GSK-3 activity in these cells. The peptides described herein can be administered via any route that is medically acceptable. The route of administration can depend on the disease, condition, organ or injury being treated. Possible administration routes include injections, by parenteral routes, such as intravascular, intravenous, intra-arterial, subcutaneous, intramuscular, intratumor, intraperitoneal, intraventricular, intraepidural, intracerebroventricular, intranasal or others, as well as via oral, nasal, ophthalmic, rectal or topical routes of administration, or by inhalation. Sustained release administration is also encompassed herein, by means such as, for example, depot injections or erodible implants, or by sustained release oral formulations (e.g., solid oral formulations). Administration can also be intra-articularly, intrarectally, intraperitoneally, intramuscularly, subcutaneously, or by aerosol inhalant. Where treatment is systemic, the peptide can be administered orally, nasally or parenterally, such as intravenously, intramuscularly, subcutaneously, intraorbitally, intracapsularly, intraperitoneally or intracisternally, as long as provided in a composition suitable for effecting the introduction of the peptide into target cells, as is detailed hereinbelow.

In some embodiments, administration is effected nasally, namely via a nasal route of administration. A nasal administration can be effected either by intranasal injection or by means of a spray or liquid formulation that is administered nasally.

The phrase "therapeutically effective amount", as used herein, describes an amount administered to an individual, which is sufficient to abrogate, substantially inhibit, slow or reverse the progression of a condition associated with GSK-3 activity, to substantially ameliorate clinical symptoms of a such a condition or substantially prevent the appearance of clinical symptoms of such a condition. The GSK-3 activity can be a GSK-3 kinase activity. The inhibitory amount may be determined directly by measuring the inhibition of a GSK-3 activity, or, for example, where the desired effect is an effect on an activity downstream of GSK-3 activity in a pathway that includes GSK-3, the inhibition may be measured by measuring a downstream effect. Thus, for example where inhibition of GSK-3 results in the arrest of phosphorylation of glycogen synthase, the effects of the peptide may include effects on an insulin-dependent or insulin-related pathway, and the peptide may be administered to the point where glucose uptake is increased to optimal levels. Also, where the inhibition of GSK-3 results in the absence of phosphorylation of a protein that is required for further biological activity, for example, the tau protein, then the peptide may be administered until polymerization of phosphorylated tau protein is substantially arrested. Level of hippocampous β-catenin are also indicative for an effect on GSK-3 activity. Therefore, the inhibition of GSK-3 activity will depend in part on the nature of the inhibited pathway or process that involves GSK-3 activity, and on the effects that inhibition of GSK-3 activity has in a given biological context.

The amount of the peptide that will constitute an inhibitory amount will vary depending on such parameters as the peptide and its potency, the half-life of the peptide in the body, the rate of progression of the disease or biological condition being treated, the responsiveness of the condition to the dose of treatment or pattern of administration, the formulation, the attending physician's assessment of the medical situation, and other relevant factors, and in general the health of the patient, and other considerations such as prior administration of other therapeutics, or co-administration of any therapeutic that will have an effect on the inhibitory activity of the peptide or that will have an effect on GSK-3 activity, or a pathway mediated by GSK-3 activity.

Although it is expected that the inhibitory amount will fall in a relatively broad range that can be determined through routine trials, an exemplary therapeutically effective amount according to the present invention is selected so as to achieve, at the treated site, an amount of the peptide that ranges between about 10 nmol and about 1000 nmol, or between about 10 nmol and about 500 nmol, or between about 100 nmol and about 400 nmol.

As is discussed in detail hereinabove, GSK-3 is involved in various biological pathways and hence, the method according to this aspect of the present invention can be used in the treatment of a variety of biological conditions, as is detailed hereinunder.

GSK-3 is involved in the insulin signaling pathway and therefore, in one example, the method according this aspect of the present invention can be used to treat any insulin-dependent condition.

By "insulin-dependent condition" it is meant any condition that is mediated by insulin and which is manifested or caused by reduced level of insulin or impaired insulin potentiation pathway. Exemplary such conditions include, but are not limited to, conditions that involve glucose intolerance and impaired glucose uptake, such as diabetes, including, for example, insulin-dependent diabetes and juvenile diabetes.

As GSK-3 inhibitors are known to inhibit differentiation of pre-adipocytes into adipocytes, in another example, the method of this aspect of the present invention can be used to treat obesity.

In yet another example, the method according to this aspect of the present invention can be used to treat diabetes including non-insulin dependent diabetes mellitus.

Diabetes mellitus is a heterogeneous primary disorder of carbohydrate metabolism with multiple etiologic factors that generally involve insulin deficiency or insulin resistance or both. Type I, juvenile onset, insulin-dependent diabetes mellitus, is present in patients with little or no endogenous insulin secretory capacity. These patients develop extreme hyperglycemia and are entirely dependent on exogenous insulin therapy for immediate survival. Type II, or adult onset, or non-insulin-dependent diabetes mellitus, occurs in patients who retain some endogenous insulin secretory capacity, but the great majority of them are both insulin deficient and insulin resistant. Approximately 95% of all diabetic patients in the United States have non-insulin dependent, Type II diabetes mellitus (NIDDM), and, therefore, this is the form of diabetes that accounts for the great majority of medical problems. Insulin resistance is an underlying characteristic feature of NIDDM and this metabolic defect leads to the diabetic syndrome. Insulin resistance can be due to insufficient insulin receptor expression, reduced insulin-binding affinity, or any abnormality at any step along the insulin signaling pathway (see U.S. Pat. No. 5,861,266).

The peptides described herein can be used to treat type II diabetes in a patient with type II diabetes as follows: a therapeutically effective amount of the peptide is administered to the patient, and clinical markers, e.g., blood sugar level, are monitored. The peptide can further be used to prevent type II diabetes in a subject as follows: a prophylactically effective amount of the peptide is administered to the patient, and a clinical marker, for example IRS-1 phosphorylation, is monitored.

Treatment of diabetes is determined by standard medical methods. A goal of diabetes treatment is to bring sugar levels down to as close to normal as is safely possible. Commonly set goals are 80-120 milligrams per deciliter (mg/dl) before meals and 100-140 mg/dl at bedtime. A particular physician may set different targets for the patent, depending on other factors, such as how often the patient has low blood sugar reactions. Useful medical tests include tests on the patient's blood and urine to determine blood sugar level, tests for glycated hemoglobin level ($HbA_{1c}$; a measure of average blood glucose levels over the past 2-3 months, normal range being 4-6%), tests for cholesterol and fat levels, and tests for urine protein level. Such tests are standard tests known to those of skill in the art (see, for example, American Diabetes Association, 1998). A successful treatment program can also be determined by having fewer patients in the program with diabetic eye disease, kidney disease, or nerve disease.

Hence, in one particular embodiment of the method according to this aspect of the present invention, there is provided a method of treating non-insulin dependent diabetes mellitus: a patient is diagnosed in the early stages of non-insulin dependent diabetes mellitus. A peptide as described herein is formulated in an enteric capsule. The patient is directed to take one tablet after each meal for the purpose of stimulating the insulin signaling pathway, and thereby controlling glucose metabolism to levels that obviate the need for administration of exogenous insulin In another example, the method according to these embodiments of the present invention can be used to treat affective disorders such as unipolar disorders (e.g., depression) and bipolar disorders (e.g., manic depression). As is demonstrated herein, the effect of the peptides as described herein was exemplified on up-regulation of β-catenin levels, thus indicating, a role of these GSK-3 inhibitors in the treatment of affective disorders.

As GSK-3 is also considered to be an important player in the pathogenesis of neurodegenerative disorders and diseases, the method according to this aspect of the present invention can be further used to treat a variety of such disorders and diseases.

In one example, since inhibition of GSK-3 results in halting neuronal cell death, the method according to these embodiments of the present invention can be used to treat a neurodegenerative disorder that results from an event that cause neuronal cell death. Such an event can be, for example, cerebral ischemia, stroke, traumatic brain injury or bacterial infection.

In another example, since GSK-3 activity is implicated in various central nervous system disorders and neurodegenerative diseases, the method according to these embodiments can be used to treat various chronic neurodegenerative diseases such as, but not limited to, Alzheimer's disease, Huntington's disease, Parkinson's disease, AIDS associated dementia, amyotrophic lateral sclerosis (AML) and multiple sclerosis.

As is discussed hereinabove, GSK-3 activity has particularly been implicated in the pathogenesis of Alzheimer's disease. Hence, in one representative embodiment of the method described herein, there is provided a method of treating a patient with Alzheimer's disease: A patient diagnosed with Alzheimer's disease is administered with a peptide as described herein, which inhibits GSK-3-mediated tau hyperphosphorylation, prepared in a formulation that crosses the blood brain barrier (BBB). The patient is monitored for tau phosphorylated polymers by periodic analysis of proteins isolated from the patient's brain cells for the presence of phosphorylated forms of tau on an SDS-PAGE gel known to characterize the presence of and progression of the disease. The dosage of the peptide is adjusted as necessary to reduce the presence of the phosphorylated forms of tau protein.

GSK-3 has also been implicated with respect to psychotic disorders such as schizophrenia, and therefore the method according to this aspect of embodiments of the present invention can be further used to treat psychotic diseases or disorders, such as schizophrenia.

GSK-3 has also been implicated with respect to affective disorders. Therefore, in another example, the method according to this aspect of the present invention can be used to treat affective disorders such as unipolar disorders (e.g., depression) and bipolar disorders (e.g., manic depression).

It should be noted that the peptides described herein are particularly advantageous in the treatment of psychotic, affective and neurodegenerative diseases or disorders since, apart from exerting enhanced inhibition activity of GSK-3, it is postulated that the inclusion of multiple hydrophobic amino acid residues within the peptides further provides for enhanced lipophilicity of the peptides and, as a result, for enhanced permeability through the blood brain barrier (BBB). This enhanced permeability may allow a systemic, rather than local, administration of the peptides, such that the need to administer the inhibitors intracerebroventicularly (icv) is avoided.

GSK-3 has also been implicated with respect to cardiovascular conditions, and therefore, the peptides described herein can be further used to treat cardiovascular diseases or disorders.

Cardiovascular diseases and disorders include, but are not limited to, atherosclerosis, a cardiac valvular disease, stenosis, restenosis, in-stent-stenosis, myocardial infarction, coronary arterial disease, acute coronary syndromes, congestive heart failure, angina pectoris, myocardial ischemia, thrombosis, Wegener's granulomatosis, Takayasu's arteritis, Kawasaki syndrome, anti-factor VIII autoimmune disease or disorder, necrotizing small vessel vasculitis, microscopic polyangiitis, Churg and Strauss syndrome, pauci-immune focal necrotizing glomerulonephritis, crescentic glomerulonephritis, antiphospholipid syndrome, antibody induced heart failure, thrombocytopenic purpura, autoimmune hemolytic anemia, cardiac autoimmunity, Chagas' disease or disorder, and anti-helper T lymphocyte autoimmunity.

GSK-3 has also been implicated with respect to conditions (e.g., infections) associated with pathogenic parasites (e.g., malaria and trypanosomiasis), and therefore, the peptides described herein can be further used to treat a condition (e.g., infection) that is associated with a presence of a pathogenic parasite in a subject. Exemplary parasites include Acanthamoeba, Anisakis, *Ascaris lumbricoides*, Botfly, *Balantidium coli*, Bedbug, Cestoda (tapeworm), Chiggers, *Cochliomyia hominivorax, Entamoeba histolytica, Fasciola hepatica, Giardia lamblia*, Hookworm, *Leishmania, Linguatula serrata*, Liver fluke, *Loa boa, Paragonimus*—lung fluke, Pinworm, *Schistosoma, Strongyloides stercoralis*, Mites, Tapeworm, *Toxoplasma gondii*, Trypanosoma, Whipworm, *Wuchereria bancrofti* and *Plasmodium falciparum* and related malaria-causing protozoan parasites.

Exemplary conditions caused by pathogenic parasites include, but are not limited to, Acanthamoeba keratitis, Amoebiasis, Ascariasis, Babesiosis, Balantidiasis, Baylisascariasis, Chagas disease, Clonorchiasis, Cochliomyia, Cryptosporidiosis, Diphyllobothriasis, Dracunculiasis (caused by the Guinea worm), Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Leishmaniasis, Lyme disease, Malaria, Metagonimiasis, Myiasis, Onchocerciasis, Pediculosis, Scabies, Schistosomiasis, Sleeping sickness, Strongyloidiasis, Taeniasis (cause of Cysticercosis), Toxocariasis, Toxoplasmosis, Trichinosis and Trichuriasis.

GSK-3 has also been suggested to be involved in stem cell maintenance and/or differentiation. Accordingly, the peptides described herein can be further utilized in the treatment of conditions in which transplantation of stem cells is used as part of the treatment. Such conditions include, for example, cancer and damaged tissues (treatable by tissue regeneration).

In some embodiments, the peptides described herein can be utilized for maintaining and/or differentiating stem cells. Thus, in some embodiments, there is provided a method of maintaining and/or differentiating stem cells, which is effected by contacting a peptide as described herein with stem cells. In some embodiments, the contacting is effected ex-vivo. In some embodiments, the contacting is effected in the presence of a physiological medium, as acceptable for stem cells preparations. In some embodiments, the contacting is effected by placing stem cells in a suitable medium which further comprises a peptide as described herein.

The method according to this aspect of the present invention can be further effected by co-administering to the subject one or more additional active ingredient(s) which is capable of altering an activity of GSK-3.

As used herein, "co-administering" describes administration of a peptide as described herein in combination with the additional active ingredient(s) (also referred to herein as active or therapeutic agent). The additional active agent can be any therapeutic agent useful for treatment of the patient's condition. The co-administration may be simultaneous, for example, by administering a mixture of the peptide and the additional therapeutic agent, or may be accomplished by administration of the peptide and the active agent separately, such as within a short time period. Co-administration also includes successive administration of the peptide and one or more of another therapeutic agent. The additional therapeutic agent or agents may be administered before or after the peptide. Dosage treatment may be a single dose schedule or a multiple dose schedule.

An example of an additional active agent is insulin.

Preferably, the additional active agent is capable of inhibiting an activity of GSK-3, such that the additional active agent can be any GSK-3 inhibitor other than the peptides described herein, and thus can be, as non-limiting examples, lithium, valproic acid and other peptides or small molecules that are shown to inhibit GSK-3 activity as described herein.

Alternatively, the additional active agent can be an agent that is capable of downregulating an expression of GSK-3.

An agent that downregulates GSK-3 expression refers to any agent which affects GSK-3 synthesis (decelerates) or degradation (accelerates) either at the level of the mRNA or at the level of the protein. For example, a small interfering polynucleotide molecule which is designed to downregulate the expression of GSK-3 can be used as an additional active agent according to some embodiments of the present invention.

An example for a small interfering polynucleotide molecule which can down-regulate the expression of GSK-3 is a small interfering RNA or siRNA, such as, for example, the morpholino antisense oligonucleotides described by in Munshi et al. (Munshi C B, Graeff R, Lee H C, *J Biol Chem* 2002 Dec. 20; 277(51):49453-8), which includes duplex oligonucleotides which direct sequence specific degradation of mRNA through the previously described mechanism of RNA interference (RNAi) (Hutvagner and Zamore (2002) Curr. Opin. Genetics and Development 12:225-232).

As used herein, the phrase "duplex oligonucleotide" refers to an oligonucleotide structure or mimetics thereof, which is formed by either a single self-complementary nucleic acid strand or by at least two complementary nucleic acid strands. The "duplex oligonucleotide" of the present invention can be composed of double-stranded RNA (dsRNA), a DNA-RNA hybrid, single-stranded RNA (ssRNA), isolated RNA (i.e., partially purified RNA, essentially pure RNA), synthetic RNA and recombinantly produced RNA.

Preferably, the specific small interfering duplex oligonucleotide of the present invention is an oligoribonucleotide composed mainly of ribonucleic acids.

Instructions for generation of duplex oligonucleotides capable of mediating RNA interference are provided in www-dotambiondotcom.

Hence, the small interfering polynucleotide molecule according to some embodiments of the present invention can be an RNAi molecule (RNA interference molecule).

Alternatively, a small interfering polynucleotide molecule can be an oligonucleotide such as a GSK-3-specific antisense molecule or a rybozyme molecule, further described hereinunder.

Antisense molecules are oligonucleotides, which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target polynucleotide. An additional region of the oligonucleotide may serve as a substrate for enzymes capable of cleaving RNA:DNA or RNA:RNA hybrids. An example for such includes RNase H, which is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

The antisense molecules of the present invention may be formed as composite structures of two or more oligonucleotides, modified oligonucleotides, as described above. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein fully incorporated by reference.

Rybozyme molecules are being increasingly used for the sequence-specific inhibition of gene expression by the cleavage of mRNAs. Several rybozyme sequences can be fused to the oligonucleotides of the present invention. These sequences include but are not limited ANGIOZYME specifically inhibiting formation of the VEGF-R (Vascular Endothelial Growth Factor receptor), a key component in the angiogenesis pathway, and HEPTAZYME, a rybozyme designed to selectively destroy Hepatitis C Virus (HCV) RNA, (Rybozyme Pharmaceuticals, Incorporated—WEB home page).

Further alternatively, a small interfering polynucleotide molecule, according to the present invention can be a DNAzyme.

DNAzymes are single-stranded catalytic nucleic acid molecules. A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M Curr Opin Mol Ther 2002; 4:119-21).

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al., 2002, Abstract 409, Ann Meeting Am Soc Gen Ther wwwdotasgtdotorg). In another application, DNAzymes complementary to bcr-ab1 oncogenes were successful in inhibiting the oncogenes expression in leukemia cells, and lessening relapse rates in autologous bone marrow transplant in cases of CML and ALL.

Oligonucleotides designed according to the teachings of the present invention can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art.

Further according to embodiments of the present invention there is provided a use of the peptides as described herein in the manufacture of a medicament for treating a biological condition associated with GSK-3 activity, as described herein.

Further according to embodiments of the present invention there is provided a peptide as described herein, which is identified for use in the treatment of a biological condition associated with GSK-3 activity, as described herein.

In any of the methods and uses described herein, the peptides described herein can be utilized in combination with one or more additional active ingredient(s) or agent(s) which is capable of altering an activity of GSK-3, as described herein.

In any of the methods and uses described herein the peptide described herein can be utilized either per se, or, preferably, the peptide forms a part of a pharmaceutical composition, which may further comprise a pharmaceutically acceptable carrier.

As used herein a "pharmaceutical composition" refers to a preparation of one or more of the peptides described herein (as active ingredient), or physiologically acceptable salts or prodrugs thereof, with other chemical components including but not limited to physiologically suitable carriers, excipients, lubricants, buffering agents, antibacterial agents, bulking agents (e.g. mannitol), antioxidants (e.g., ascorbic acid or sodium bisulfite), anti-inflammatory agents, anti-viral agents, chemotherapeutic agents, anti-histamines and the like. The purpose of a pharmaceutical composition is to facilitate administration of a compound to a subject.

The term "active ingredient", which is also referred to herein interchangeably as "active agent" refers to a compound, which is accountable for a biological effect.

The terms "physiologically acceptable carrier" and "pharmaceutically acceptable carrier" which may be interchangeably used refer to a carrier or a diluent that does not cause significant irritation to an organism and does not abrogate the biological activity and properties of the administered compound.

Herein the term "excipient" refers to an inert substance added to a pharmaceutical composition to further facilitate administration of a drug. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences" Mack Publishing Co., Easton, Pa., latest edition, which is incorporated herein by reference.

Pharmaceutical compositions for use in accordance with the present invention thus may be formulated in conventional manner using one or more pharmaceutically acceptable carriers comprising excipients and auxiliaries, which facilitate processing of the compounds into preparations which can be used pharmaceutically. Proper formulation is dependent upon the route of administration chosen. The dosage may vary depending upon the dosage form employed and the route of administration utilized. The exact formulation, route of administration and dosage can be chosen by the individual physician in view of the patient's condition (see e.g., Fingl et al., 1975, in "The Pharmacological Basis of Therapeutics", Ch. 1 p. 1).

The pharmaceutical composition may be formulated for administration in either one or more of routes depending on whether local or systemic treatment or administration is of choice, and on the area to be treated. Administration may be done orally, nasally, by inhalation, or parenterally, for example by intravenous drip or intraperitoneal, subcutaneous, intramuscular or intravenous injection, or topically (including ophtalmically, vaginally, rectally and intranasally).

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, pills, caplets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives. Slow release compositions are envisaged for treatment.

In some embodiments, there is provided a pharmaceutical composition, as described herein, being formulated for nasal administration, as defined herein.

The amount of a composition to be administered will, of course, be dependent on the subject being treated, the severity of the affliction, the manner of administration, the judgment of the prescribing physician, etc.

The pharmaceutical composition may further comprise additional pharmaceutically active or inactive agents such as, but not limited to, an anti-bacterial agent, an antioxidant, a buffering agent, a bulking agent, a surfactant, an anti-inflammatory agent, an anti-viral agent, a chemotherapeutic agent and an anti-histamine.

According to an embodiment of the present invention, the pharmaceutical composition described herein is packaged in a packaging material and identified in print, in or on the packaging material, for use in the treatment of a medical condition associated with GSK-3 activity, as described herein.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

In some embodiments, the pharmaceutical composition is identified for use in combination with an additional active agent, as described herein.

In some embodiments, the pharmaceutical composition further comprises an additional active agent as described herein, being co-formulated with the peptide as described herein.

Further according to embodiments of the present invention there is provided a use of any of the peptides and/or the GSK-3 substrate competitive inhibitors as described herein in the manufacture of a medicament for treating a biological condition associated with GSK-3 activity, as described herein.

Further according to embodiments of the present invention there is provided a method of treating a biological condition associated with GSK-3 activity, as described herein, an/or of inhibiting a GSK-3 activity, which is effected by administering to a subject in need thereof any of the GSK-3 substrate competitive inhibitors as described herein.

Further according to embodiments of the present invention there is provided a GSK-3 substrate competitive inhibitor and/or a peptide as described herein, which is identified for use in the treatment of a biological condition associated with GSK-3 activity, as described herein.

In any of the methods and uses described herein the GSK-3 substrate competitive inhibitors as described herein can be utilized either per se, or, preferably, or forms a part of a pharmaceutical composition, which may further comprise a pharmaceutically acceptable carrier, as described herein.

As described herein, in the course of the studies conducted for designing GSK-3 substrate competitive inhibitors with improved performance, the present inventors have prepared various mutants of GSK-3β. Such mutants served as a tool for identifying potential inhibitors of GSK-3 activity.

These mutants included pre-determined modifications at a subunit of the catalytic binding site of GSK-3, previously described as the 89-95 loop, as set forth in SEQ ID NO:2.

Thus, according to an aspect of some embodiments of the present invention there is provided a polypeptide which comprises an amino acid sequence of a mutated GSK-3 enzyme, wherein an amino acid sequence of mutated GSK-3 enzyme comprises at least one amino acid substitution with respect to an amino acid sequence of a catalytic binding site of a wild-type GSK-3.

The "mutated GSK-3 enzyme" of these embodiments of the present invention refers to a polypeptide which differs from a corresponding wild-type GSK-3 (i.e., the starting point GSK-3) by at least one mutation (e.g., substitution).

A wild-type GSK-3 is as defined hereinabove for GSK-3.

In some embodiments, the mutated GSK-3 enzyme is characterized by a substrate specificity which is substantially identical to that of a respective wild-type GSK-3.

According to some embodiments, the mutated enzyme comprises at least one amino acid substitution with respect to an amino acid sequence of a subunit of the catalytic (substrate's) binding site of the corresponding wild-type GSK-3.

According to some embodiments of the present invention, the subunit of the substrate's binding site of a wild-type GSK-3 comprises positions 89-95 of the amino acid sequence of the wild-type GSK-3, and has an amino acid sequence as set forth in SEQ ID NO:2. This subunit is also referred to herein as a 89-95 subunit or a 89-95 loop.

According to some embodiments of the present invention, the amino acid substitution is at one or more of positions 89, 90, 91, 92, 93, 94 and/or 95 of the 89-95 subunit. In most of the living organisms expressing GSK-3, these positions correspond to Q89 (Gln89), R92 (Arg92), F93 (Phe93), K94 (Lys94), and N95 (Asn95), as is in e.g., human GSK-3β. Thus, according to an aspect of some embodiments of the present invention there is provided a polypeptide which comprises an amino acid sequence of a mutated GSK-3 enzyme, wherein an amino acid sequence of the mutated GSK-3 enzyme comprises at least one amino acid substitution with respect to position Gln89, Asp90, Lys91, Arg92, Phe93, Lys94 and/or Asn95 of a corresponding wild-type GSK-3 (e.g., having an amino acid sequence as set forth in SEQ ID NO:1).

Thus, according to an aspect of some embodiments of the present invention there is provided a polypeptide which comprises an amino acid sequence of a mutated GSK-3 enzyme, wherein an amino acid sequence of the mutated GSK-3 enzyme comprises an amino acid substitution with respect to position Val214, or an equivalent thereof of a corresponding wild-type GSK-3 (e.g., having an amino acid sequence as set forth in SEQ ID NO:1).

Herein throughout, whenever a three-letter abbreviation of an amino acid is followed by a number it is meant the number of the indicated amino acid residue along the amino acid sequence downstream the N-terminus of the enzyme. The three-letter abbreviations described herein are as commonly used in the art.

By "position" it is meant a coordinate of the amino acid, whereby the indicated coordinate encompasses also an amino acid equivalent, as defined herein.

According to some embodiments of the present invention, the amino acid substitution comprises an alanine substitution such that one or more of the amino acids at positions 89, 92, 93, 94 and 95, or at position 214 of a wild-type GSK-3 is substituted by an alanine residue. However, substitution by any other amino acid residue is also contemplated.

The mutated GSK-3 enzyme is thus characterized by at least one amino acid substitution with respect to an amino acid sequence of a corresponding wild type GSK-3.

Exemplary polypeptides according to some embodiments of the present invention comprise an amino acid sequence at positions 89-95 as set forth in SEQ ID NOS:6-10 and 47.

The present embodiments also encompass functional homologues of the polypeptides described herein, such homologues can be at least 50%, at least 55%, at least 60%, at least 65%, at least 70%, at least 75%, at least 80%, at least 85%, at least 95% or more say 100% homologous to SEQ ID NOS:6-10 and 47, as long as the indicated substitution is maintained.

In some embodiments, the polypeptides described herein are phosphorylated. In some embodiments, the polypeptides described herein comprise an amino acid sequence in which Tyr 216 or an equivalent thereof is phosphorylated.

Recombinant techniques, as described herein, are preferably used to generate the polypeptides of the present invention. Alternatively, the polypeptides are prepared by chemical synthesis, using, for example, solid phase synthesis as described herein.

Thus, further according to an aspect of some embodiments of the present invention there is provided a polynucleotide encoding the isolated polypeptide as described herein.

As used herein the term "polynucleotide" refers to a single or a double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

According to some embodiments, the nucleic acid sequence which encodes the mutated GSK-3 enzyme is of a mammalian origin, such as a mouse origin, a human origin, a rat origin, a rabbit origin or a combination thereof (e.g., a result of gene shuffling), and is preferably of a human origin.

To produce a polypeptide of the present invention using recombinant technology, a polynucleotide encoding the polypeptide as described herein is ligated into a nucleic acid expression construct, which includes the polynucleotide sequence under the transcriptional control of a promoter sequence suitable for directing constitutive or inducible transcription in the host cells, as further described hereinbelow.

Other than containing the necessary elements for the transcription and translation of the inserted coding sequence, the expression construct of the present invention can also include sequences (i.e., tags) engineered to enhance stability, production, purification, yield or toxicity of the expressed polypeptide. Such a fusion protein can be designed so that the fusion protein can be readily isolated by affinity chromatography; e.g., by immobilization on a column specific for the heterologous protein. Where a cleavage site is engineered between the peptide moiety and the heterologous protein, the peptide can be released from the chromatographic column by treatment with an appropriate enzyme or agent that disrupts the cleavage site [e.g., see Booth et al. (1988) Immunol. Lett. 19:65-70; and Gardella et al., (1990) J. Biol. Chem. 265:15854-15859].

A variety of prokaryotic or eukaryotic cells can be used as host-expression systems to express the peptide coding sequence. These include, but are not limited to, microorganisms, such as bacteria transformed with a recombinant bacteriophage DNA, plasmid DNA or cosmid DNA expression vector containing the peptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence. Mammalian expression systems can also be used to express the peptides of the present invention. Bacterial systems are preferably used to produce recombinant polypeptides, according to the present invention, thereby enabling a high production volume at low cost.

Other expression systems such as insects and mammalian host cell systems, which are well known in the art can also be used by the present invention.

In any case, transformed cells are cultured under effective conditions, which allow for the expression of high amounts of recombinant polypeptides. Effective culture conditions include, but are not limited to, effective media, bioreactor, temperature, pH and oxygen conditions that permit protein production. An effective medium refers to any medium in which a cell is cultured to produce the recombinant peptides of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art (see Example 1 of the Examples section).

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

Following a certain time in culture, recovery of the recombinant protein is effected. The phrase "recovering the recombinant protein" refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Thus, further according to embodiments of the present invention there is provided a nucleic acid construct comprising the polynucleotide as described herein.

Further according to embodiments of the present invention there is provided a host cell system comprising the nucleic acid construct as described herein.

The polypeptides described herein can be utilized in a screening method for identifying putative GSK-3 substrate competitive inhibitors. Since it has been demonstrated herein that the mutated polypeptides lack those coordinates that provide for increased binding to the substrate's binding site in GSK-3, it is suggested that when a candidate inhibitor exhibits a reduced effect on the activity of a mutated enzyme, compared to its effect on a corresponding wild-type GSK-3, such a candidate is characterized by strong affinity to the lacking coordinate and thus could serve as a potent substrate competitive inhibitor. It is to be noted that potent substrate competitive inhibitors should not only exhibit binding to the substrate's binding site of the enzyme, but should exhibit such a binding that is at least similar, and preferably stronger than that of a GSK-3 substrate.

Thus, according to an aspect of some embodiments of the present invention there is provided a method of identifying a putative GSK-3 substrate competitive inhibitor. In some embodiments, the method is effected by screening a plurality of substances for a substance which exhibits inhibition of at least 20% of an activity of a wild-type GSK-3 enzyme and which exhibits inhibition of no more than 20% of an activity of the polypeptide which comprises an amino acid sequence of a mutated GSK-3, as described herein.

By "putative" it is meant capable of reducing an activity of a GSK-3 enzyme by at least 10%, at least 20%, at least 30%, at least 40%, at least 50%, and so forth, up to 100%, including any intermediate value, as determined by methods known in the art for determining a catalytic activity of a kinase, and as if further detailed hereinbelow. In some embodiments, reducing the activity of a GSK-3 by the substance is effected by competing with the substrate on the binding to the catalytic site of the enzyme. Determining a substrate competitive nature of an inhibitor can be performed by methods known in the art.

In some embodiments, the screening is effected by determining a level of inhibition of a wild-type GSK-3 enzyme by each of the tested substance; determining a level of inhibition of a polypeptide which comprises a mutated GSK-3 enzyme as described herein by each of the tested substance; and comparing these levels of inhibition for each substance. Those substances that substantially inhibit an activity of a wild-type GSK-3 but substantially lack an inhibition activity of a mutated GSK-3, as in the polypeptides described herein, are considered putative GSK-3 substrate competitive inhibitors.

By "substantially inhibiting an activity of a wild-type GSK-3" it is meant that a phosphorylation of a GSK-3 substrate in the presence of the tested substance is lower than the phosphorylation in the absence of the tested compound by at least 20%, or at least 30%, or at least 40%, or at least 50%, or at least 60%, or at least 70%, or at least 80%, or at least 90 5, and even by 100%.

By substantially lacking an inhibition activity it is meant that a phosphorylation of a mutated GSK-3 substrate in the presence of the tested substance is substantially the same as the phosphorylation in the absence of the tested compound, or is lower by no more than 1%, or 5%, or 10%, or 12%, or 15% and in any case by no more than 20%.

In some embodiments, a substance identified as a putative inhibitor exhibits inhibition of at least 50% of a wild-type GSK-3 enzyme and an inhibition of less than 10% of an activity of a mutated GSK-3 enzyme.

Determining an activity of a GSK-3 enzyme or of a mutant thereof can be performed by any method known in the art for assaying a kinase activity (e.g., phosphorylation). In some embodiments an activity of a GSK-3 enzyme is determined by contacting the enzyme with a GSK-3 substrate, as described herein, in a suitable medium, and determining a level of a phosphorylated substrate thereafter. An inhibition activity of a substance can be readily determined by contacting the enzyme with a GSK-3 substrate and with the tested substance, as described herein, in a suitable medium, and determining a level of a phosphorylated substrate thereafter. The ratio (e.g., percentage) between the level of phosphorylation of the substrate in the presence and absence of the tested compound is indicative of the level of inhibition exhibited by the tested substance.

Similarly, according to another aspect of some embodiments of the present invention there is provided a method of identifying a putative substrate competitive inhibitor of GSK-3, which is effected by screening a plurality of substances for a substance which exhibits inhibition of at least 20% of an activity of a wild-type GSK-3 enzyme and which exhibits inhibition of less than 20% of said activity of a mutated GSK-3 enzyme, wherein the mutated GSK-3 enzyme comprises at least one amino acid substitution with respect to position Asp90, Lys91, Arg92, Phe93 and/or Lys94 or to position Val214 of a corresponding wild-type GSK3 enzyme, as described herein, and, for example, as set forth in SEQ ID NOS:6-10 and 47.

In some embodiments, the mutated GSK-3 enzyme comprises at least one amino acid substitution with respect to position Asp90, Arg92, Phe93 and/or Lys94 of a corresponding wild-type GSK3 enzyme, for example, as set forth in SEQ ID NOS:6 AND 8-10).

In some embodiments, the mutated GSK-3 enzyme comprises an amino acid substitution with respect to position Phe93 of said corresponding wild-type GSK-3 enzyme, for example, as set forth in SEQ ID NO:9.

In any of the screening methods described herein, the tested substances can be peptides, polypeptides and/or small organic molecules, as defined herein.

The experimental identification of Phe93 as an important binding site within the substrate's binding subunit of a GSK-3 enzyme, can be further utilized in in silico screening for a putative substrate competitive inhibitor.

Thus, according to an aspect of some embodiments of the present invention there is provided another method of identifying a putative substrate competitive inhibitor of GSK-3. In some embodiments, this method is effected by screening a plurality of substances for a substance capable of interacting with a Phe93 residue, or an equivalent amino acid thereof, in a catalytic binding site of a GSK-3 enzyme.

In some embodiments, the method is effected by determining the binding of a candidate substance to Phe93 or an equivalent thereof in GSK-3 by comparing the inhibition of an activity of a wild-type GSK-3 as exhibited by the substance to an inhibition of an activity of a mutated GSK-3 that comprises an amino acid substitution with respect to Phe93, as described herein, as exhibited by the substance.

Such a method is effected as described hereinabove, while utilizing, for example, a polypeptide that comprises a mutated enzyme as set forth in SEQ ID NO:9.

In some embodiments, the method comprises computationally screening the plurality of substances for a substance capable of interacting with phenylalanine at coordinate 93, or with an equivalent amino acid thereof, within a set of atomic structural coordinates defining a three-dimensional atomic structure of a catalytic binding site of GSK-3 (e.g., a GSK-3 as set forth in SEQ ID NO:1).

In some embodiments, the method is further effected by identifying a substance that is further capable, in addition to interacting with Phe93, of interacting with at least one additional amino acid within the catalytic binding site of a GSK-3.

In some embodiments, the additional amino acid is one or more of Phe67, Gln89, Asp90, Lys91, Arg92, Lys94 and Asp95 in a GSK-3 enzyme (e.g., wild-type GSK-3 enzyme such as human GSK-3β.

In some embodiments, the additional amino acid is one or more of Phe67, Gln89, Asp90, Arg92, Lys 94 and Asp95 in a GSK-3 enzyme (e.g., wild-type GSK-3 enzyme such as human GSK-3β.

In some embodiments, the additional amino acid is one or more of Phe67, Gln89 and Asn95 (e.g., wild-type GSK-3 enzyme such as human GSK-3β.

In some embodiments, the additional amino acid is one or more of any of the amino acids identified hitherto with respect to substrate's binding in GSK-3, as delineated hereinabove.

The method of these embodiments of the present invention is generally effected by constructing a model using a set of atomic structural coordinates defining a three-dimensional atomic structure of GSK-3 and computationally screening a plurality of substances, as described herein, for a substance capable of interacting with Phe93, to thereby identify the GSK-3 inhibitor.

Typically, obtaining the set of atomic coordinates which define the three dimensional structure of an enzyme can be effected using various approaches which are well known in the art.

Structural data obtained is preferably recorded on a computer readable medium so as to enable data manipulation and construction of computational models. As used herein, "computer readable medium" refers to any medium which can be read and accessed directly by a computer. Such media include, but are not limited to, magnetic storage media, such as floppy discs, hard disc storage medium, and magnetic tape; optical storage media such as optical discs or CD-ROM; electrical storage media such as RAM and ROM; and hybrids of these categories such as magnetic/optical storage media. Selection and use of appropriate storage media is well within the capabilities of one of ordinary skill in the art.

As used herein, "recorded" refers to a process of storing information on computer readable medium.

It will be appreciated that a number of data storage devices can be used for creating a computer readable medium having recorded thereon the structural data of the present invention. The choice of the data storage structure is typically based on the means chosen to access the stored information. In addition, a variety of data processor programs and formats can be used to store the data information of the present invention on computer readable medium. The sequence information can be represented in a word processing text file, formatted in commercially-available software such as WordPerfect and MICROSOFT Word, or represented in the form of an ASCII file, stored in a database application, such as DB2, Sybase, Oracle, or the like.

It will be appreciated that structure models are preferably generated by a computing platform, which generates a graphic output of the models via a display generating device such as screen or printer. The computing platform generates graphic representations of atomic structure models via a processing unit which processes structure coordinate data stored in a retrievable format in the data storage device.

Suitable software applications, well known to those of skill in the art, which may be used by the processing unit to process structure coordinate data so as to provide a graphic output of three-dimensional structure models generated therewith via display include, for example, RIBBONS (Carson, M., 1997. Methods in Enzymology 277, 25), O (Jones, T A. et al., 1991. Acta Crystallogr A47, 110), DINO (DINO: Visualizing Structural Biology (2001) wwwdotdino3ddotorg); and QUANTA, CHARMM, INSIGHT, SYBYL, MACROMODE, ICM, MOLMOL, RASMOL and GRASP (reviewed in Kraulis, J., 1991. Appl Crystallogr. 24, 946).

As mentioned hereinabove, once a structural model of GSK-1 is obtained substances which specifically bind the Phe93 residue in the active site of the model are identifiable. This is preferably effected using Rational Drug Design (RDD).

One approach to identify a putative inhibitor via rational drug design is by screening a chemical and/or peptide structure database ("3D database"), using software employing "scanner" type algorithms. Such software applications utilize atomic coordinates defining the three-dimensional structure of a binding pocket of a molecule and of a chemical structure stored in the database to computationally model the "docking" of the screened chemical structure with the binding pocket so as to qualify the binding of the binding pocket, or of the indicated amino acid therein, with the chemical structure. Iterating this process with each of a plurality of chemical structures stored in the database therefore enables computational screening of such a plurality to identify a chemical structure potentially having a desired binding interaction with the binding pocket, or with the indicated amino acid residue therein, and hence the putative inhibitor.

Any commercially available library of chemical structures of small molecules and/or peptides can be used as a suitable chemical structure database for identifying the inhibitor as described herein.

Alternatively, identifying the inhibitor can be effected using de novo rational drug design, or via modification of a known chemical structure. In such case, software comprising "builder" type algorithms utilizes a set of atomic coordinates defining a three-dimensional structure of the binding pocket and the three-dimensional structures of basic chemical building blocks to computationally assemble a putative inhibitor. Such an approach may be employed to structurally refine a putative inhibitor identified, for example, via chemical database screening as described above.

Ample guidance for performing rational drug design by utilizing software employing such "scanner" and "builder" type algorithms is available in the literature.

Criteria employed by software programs used in rational drug design to qualify the binding of screened chemical structures with binding pockets include gap space, hydrogen bonding, electrostatic interactions, van der Waals forces, hydrophilicity/hydrophobicity, etc. Generally, the greater the contact area between the screened substance and the indicated binding site of the enzyme, the lower the steric hindrance, the lower the "gap space", and the greater the number of at least the hydrophobic interactions, the greater will be the capacity of the screened substance to bind to the indicated amino acid residue within the binding site of GSK-3.

The "gap space" refers to unoccupied space between the van der Waals surface of a screened substance positioned within a binding pocket and the surface of the binding pocket defined by amino acid residues in the binding pocket. Gap space may be identified, for example, using an algorithm based on a series of cubic grids surrounding the docked molecule.

Modeling or docking may be followed by energy minimization with standard molecular mechanics force fields or dynamics with programs known in the art.

In some embodiments, once a putative substance is identified in silico, it is further tested by "wet" experiments, by determining, in vitro, an inhibition of an activity of GSK-3 by the substance, as described herein.

In some embodiments, in order to further substantiate that the substance is an effective substrate-competitive inhibitor, its binding to Phe93 is determined by comparing an inhibition of an activity of a wild-type GSK-3 to an inhibition of an activity of a mutated GSK-3 that comprises an amino acid substitution with respect to Phe93 (e.g., as set forth in SEQ ID NO:9), as described herein.

Thus, a substance that (i) is in silico identified suitable to bind Phe93 in a GSK-3 enzyme; (ii) inhibits an activity of GSK-3 in in vitro assays for determining a kinase activity in the presence and absence of the substance; and (iii) inhibits an activity of a Phe93-mutated GSK-3 enzyme by less than 20%, is identified as a putative (potent) GSK-3 substrate competitive inhibitor.

General:

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the terms "polypeptide" and "peptide" encompass an amino acid sequence of any length including full-length proteins or portions thereof, wherein the amino acid residues are linked by covalent peptide bonds. Generally, an amino acid sequence of 50 amino acids and more are referred to herein as "polypeptide" or "protein", and an amino acid sequence of less than 50 amino acids is referred to herein as "peptide".

The term "peptide" as used herein encompasses also peptoids and semipeptoids which are peptide analogs, which may have, for example, modifications rendering the peptides more stable while in a body or more capable of penetrating into cells. Such modifications include, but are not limited to N-terminus modification, C-terminus modification, peptide bond modification, including, but not limited to, $CH_2$—NH, $CH_2$—S, $CH_2$—S═O, O═C—NH, $CH_2$—O, $CH_2$—$CH_2$, S═C—NH, CH═CH or CF═CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

In some embodiments, the peptides described herein are chemically synthesized peptides.

Peptide bonds (—CO—NH—) within the peptide may be substituted, for example, by N-methylated bonds (—N($CH_3$)—CO—), ester bonds (—C(R)H—C—O—O—C(R)—N—), ketomethylen bonds (—CO—$CH_2$—), α-aza bonds (—NH—N(R)—CO—), wherein R is any alkyl, e.g., methyl, carba bonds (—$CH_2$—NH—), hydroxyethylene bonds (—CH(OH)—$CH_2$—), thioamide bonds (—CS—NH—), olefinic double bonds (—CH═CH—), retro amide bonds (—NH—CO—), peptide derivatives (—N(R)—$CH_2$—CO—), wherein R is the "normal" side chain, naturally presented on the carbon atom.

These modifications can occur at any of the bonds along the peptide chain and even at several (2-3) at the same time.

As used herein, the phrase "amino acid residue", which is also referred to herein, interchangeably, as "amino acid", describes an amino acid unit within a polypeptide chain. The amino acid residues within the peptides described herein can be either natural or modified amino acid residues, as these phrases are defined hereinafter.

As used herein, the phrase "natural amino acid residue" describes an amino acid residue, as this term is defined hereinabove, which includes one of the twenty amino acids found in nature.

As used herein, the phrase "modified amino acid residue" describes an amino acid residue, as this term is defined hereinabove, which includes a natural amino acid that was subjected to a modification at its side chain. Such modifications are well known in the art and include, for example, incorporation of a functionality group such as, but not limited to, a hydroxy group, an amino group, a carboxy group and a phosphate group within the side chain. This phrase therefore includes, unless otherwise specifically indicated, chemically modified amino acids, including amino acid analogs (such as penicillamine, 3-mercapto-D-valine), naturally-occurring non-proteogenic amino acids (such as norleucine), and chemically-synthesized compounds that have properties known in the art to be characteristic of an amino acid. The term "proteogenic" indicates that the amino acid can be incorporated into a protein in a cell through well-known metabolic pathways.

Accordingly, as used herein, the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids which are linked via a peptide bond or a peptide bond analog to at least one addition amino acid as this term is defined herein.

The peptides of the present embodiments are preferably utilized in a linear form, although it will be appreciated that in cases where cyclization does not severely interfere with peptide characteristics, cyclic forms of the peptide can also be utilized).

Cyclic peptides can either be synthesized in a cyclic form or configured so as to assume a cyclic form under desired conditions (e.g., physiological conditions).

The peptides of the present embodiments are preferably peptidomimetics, as this term is define hereinabove, which mimic the structural features of the critical amino acid motif $ZX_1X_2X_3S(p)$, as is further detailed hereinabove.

Protein phosphorylation plays a crucial part in the biochemical control of cellular activity. Phosphorylation usually means formation of a phosphate ester bond between a phosphate ($PO_4$) group and an amino acid containing a hydroxyl (OH) group (tyrosine, serine and threonine). Many phosphorylation sites in proteins act as recognition elements for binding to other proteins, and those binding events activate or deactivate signaling and other pathways. Protein phosphorylation thus acts as a switch to turn biochemical signaling on and off.

Phosphopeptide mimetics are a subclass of peptidomimetics that contain analogs of phosphorylated tyrosine, serine and threonine. Phosphate esters may be hydrolyzed by various enzymes, thus turning off a phosphorylation signal. Phosphopeptide mimetics, however, usually contain non-hydrolyzable analogs to prevent inactivation (Burke et al, 1994a; Burke et al, 1996a; Chen et al, 1995; Wiemann et al, 2000; Shapiro et al, 1997; Otaka et al, 1995; Otaka et al, 2000). General examples of phosphopeptide mimetics in the art include SH2 domain analogs (Burke et al, 1994a; Fu et al, 1998; Gao et al, 2000; Mikol et al, 1995; Ye et al, 1995), transcription factor NF-(kappa)B analog (McKinsey et al, 1997), P53 analog (Higashimoto et al, 2000) and protein-tyrosine phosphatase inhibitors (Burke et al, 1994b; Burke et al, 1996b; Groves et al, 1998; Kole et al, 1995; Kole et al, 1997; Roller et al, 1998).

Commercially available software packages can be used to design small peptides and/or peptidomimetics containing, phosphoserine or phosphothreonine analogs, preferably non-hydrolyzable analogs, as specific antagonists/inhibitors. Suitable commercially available software for analyzing crystal structure, designing and optimizing small peptides and peptidomimetics include, but are not limited to: Macromolecular X-ray Crystallography QUANTA Environment (Molecular Simulations, Inc.); TeXsan, BioteX, and SQUASH (Molecular Structure Corporation); and Crystallographica (Oxford Cryostsystems).

The peptides according to the present embodiments can further include salts and chemical derivatives of the peptides. As used herein, the phrase "chemical derivative" describes a peptide as described herein having one or more residues chemically derivatized by reaction of a functional side group. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. Also included as chemical derivatives are those peptides that contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine. The chemical derivatization does not comprehend changes in functional groups which change one amino acid to another.

As is mentioned hereinabove, some useful modifications are designed to increase the stability of the peptide in solution and, therefore, serve to prolong the half-life of the peptide in solutions, particularly biological fluids, such as blood, plasma or serum, by blocking proteolytic activity in the blood. Hence, the peptides described herein can have a stabilizing group at one or both termini. Typical stabilizing groups include amido, acetyl, benzyl, phenyl, tosyl, alkoxycarbonyl, alkyl carbonyl, benzyloxycarbonyl and the like end group modifications. Additional modifications include using one or more "D" amino acids in place of "L" amino acid(s), cyclization of the peptide inhibitor, and amide rather than amino or carboxy termini to inhibit exopeptidase activity.

The peptides described herein may or may not be glycosylated. The peptides are not glycosylated, for example, when produced directly by peptide synthesis techniques or are produced in a prokaryotic cell transformed with a recombinant polynucleotide. Eukaryotically-produced peptide molecules are typically glycosylated. The term "hydrocarbon", as used herein, encompasses any moiety that is based on a linear and/or cyclic chain of carbons which are mainly substituted by hydrogens. A hydrocarbon can be a saturated or unsaturated moiety, and can optionally be substituted by one or more substituents, as described herein.

The term "alkyl" describes a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 2 to 10 carbon atoms. Most preferably, unless otherwise indicated, the alkyl is a lower alkyl having 2 to 6 carbon atoms. The alkyl group may be substituted or unsubstituted, as defined herein.

The term "cycloalkyl" describes an all-carbon monocyclic or fused ring (i.e., rings which share an adjacent pair of carbon atoms) group where one or more of the rings does not have a completely conjugated pi-electron system. The cycloalkyl group may be substituted or unsubstituted.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. Representative examples are piperidine, piperazine, tetrahydrofurane, tetrahydropyrane, morpholino and the like.

The term "aryl" describes an all-carbon monocyclic or fused-ring polycyclic (i.e., rings which share adjacent pairs of carbon atoms) groups having a completely conjugated pi-electron system. The aryl group may be substituted or unsubstituted.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted.

Whenever an alkyl, cycloalkyl, heteroalicyclic, aryl, heteroaryl or a hydrocarbon is substituted by one or more substituents, each substituent group can independently be, for example, hydroxyalkyl, trihaloalkyl, cycloalkyl, alkenyl, alkynyl, aryl, heteroaryl, heteroalicyclic, amine, halide, sulfonate, sulfoxide, phosphonate, hydroxy, alkoxy, aryloxy, thiohydroxy, thioalkoxy, thioaryloxy, cyano, nitro, azo, sulfonamide, C-carboxylate, O-carboxylate, N-thiocarbamate, O-thiocarbamate, urea, thiourea, N-carbamate, O-carbamate, C-amide, N-amide, guanyl, guanidine and hydrazine.

A "hydroxy" group refers to an —OH group.

An "azide" group refers to a $—N{=}N^{+}{=}N^{-}$ group.

An "alkoxy" group refers to both an —O-alkyl and an —O-cycloalkyl group, as defined herein.

An "aryloxy" group refers to both an —O-aryl and an —O-heteroaryl group, as defined herein.

A "thiohydroxy" or "thiol" group refers to a —SH group.

A "thioalkoxy" group refers to both an —S-alkyl group, and an —S-cycloalkyl group, as defined herein.

A "thioaryloxy" group refers to both an —S-aryl and an —S-heteroaryl group, as defined herein.

A "carbonyl" group refers to a —C(═O)—R' group, where R' is defined as hereinabove.

A "thiocarbonyl" group refers to a —C(═S)—R' group, where R' is as defined herein.

A "C-carboxy" group refers to a —C(═O)—O—R' groups, where R' is as defined herein.

An "O-carboxy" group refers to an R'C(═O)—O— group, where R' is as defined herein.

An "oxo" group refers to a ═O group.

A "carboxylate" or "carboxyl" encompasses both C-carboxy and O-carboxy groups, as defined herein.

A "carboxylic acid" group refers to a C-carboxy group in which R' is hydrogen.

A "thiocarboxy" or "thiocarboxylate" group refers to both —C(═S)—O—R' and —O—C(═S)R' groups.

An "ester" refers to a C-carboxy group wherein R' is not hydrogen.

An ester bond refers to a —O—C(═O)— bond.

A "halo" group refers to fluorine, chlorine, bromine or iodine.

A "sulfinyl" group refers to an —S(═O)—R' group, where R' is as defined herein.

A "sulfonyl" group refers to an $—S(=O)_2—R'$ group, where R' is as defined herein.

A "sulfonate" group refers to an $—S(=O)_2—O—R'$ group, where R' is as defined herein.

A "sulfate" group refers to an $—O—S(=O)_2—O—R'$ group, where R' is as defined as herein.

A "sulfonamide" or "sulfonamido" group encompasses both S-sulfonamido and N-sulfonamido groups, as defined herein.

An "S-sulfonamido" group refers to a $—S(=O)_2—NR'R''$ group, with each of R' and R" as defined herein.

An "N-sulfonamido" group refers to an $R'S(=O)_2—NR''$ group, where each of R' and R" is as defined herein.

An "O-carbamyl" group refers to an —OC(═O)—NR'R" group, where each of R' and R" is as defined herein.

An "N-carbamyl" group refers to an R'OC(═O)—NR"— group, where each of R' and R" is as defined herein.

A "carbamyl" or "carbamate" group encompasses O-carbamyl and N-carbamyl groups.

A carbamate bond describes a —O—C(═O)—NR'— bond, where R' is as described herein.

An "O-thiocarbamyl" group refers to an —OC(═S)—NR'R" group, where each of R' and R" is as defined herein.

An "N-thiocarbamyl" group refers to an R'OC(═S)NR"— group, where each of R' and R" is as defined herein.

A "thiocarbamyl" or "thiocarbamate" group encompasses O-thiocarbamyl and N-thiocarbamyl groups.

A thiocarbamate bond describes a —O—C(═S)—NR'— bond, where R' is as described herein.

A "C-amido" group refers to a —C(═O)—NR'R" group, where each of R' and R" is as defined herein.

An "N-amido" group refers to an R'C(═O)—NR"— group, where each of R' and R" is as defined herein.

An "amide" group encompasses both C-amido and N-amido groups.

An amide bond describes a —NR'—C(═O)— bond, where R' is as defined herein.

A "urea" group refers to an —N(R')—C(═O)—NR"R'" group, where each of R' and R" is as defined herein, and R'" is defined as R' and R" are defined herein.

A "nitro" group refers to an $—NO_2$ group.

A "cyano" group refers to a —C≡N group.

The term "phosphonyl" or "phosphonate" describes a —P(═O)(OR')(OR") group, with R' and R" as defined hereinabove.

The term "phosphate" describes an —O—P(═O)(OR')(OR") group, with each of R' and R" as defined hereinabove.

A "phosphoric acid" is a phosphate group is which each of R is hydrogen.

The term "phosphinyl" describes a —PR'R" group, with each of R' and R" as defined hereinabove.

The term "thiourea" describes a —N(R')—C(=S)—NR"— group, with each of R' and R" as defined hereinabove.

Any of the substances described herein (e.g., peptides, polypeptides or small molecules), can be in a form of a pharmaceutically acceptable salt thereof.

The phrase "pharmaceutically acceptable salt" refers to a charged species of the parent compound and its counter ion, which is typically used to modify the solubility characteristics of the parent compound and/or to reduce any significant irritation to an organism by the parent compound, while not abrogating the biological activity and properties of the administered compound.

The present invention further encompasses prodrugs, solvates and hydrates of the substances described herein.

As used herein, the term "prodrug" refers to an agent, which is converted into the active compound (the active parent drug) in vivo. Prodrugs are typically useful for facilitating the administration of the parent drug. They may, for instance, be bioavailable by oral administration whereas the parent drug is not. The prodrug may also have improved solubility as compared with the parent drug in pharmaceutical compositions. Prodrugs are also often used to achieve a sustained release of the active compound in vivo. An example, without limitation, of a prodrug would be a peptide, as described herein, having one or more carboxylic acid moieties, which is administered as an ester (the "prodrug"). Such a prodrug is hydrolysed in vivo, to thereby provide the free compound (the parent drug). The selected ester may affect both the solubility characteristics and the hydrolysis rate of the prodrug.

The term "solvate" refers to a complex of variable stoichiometry (e.g., di-, tri-, tetra-, penta-, hexa-, and so on), which is formed by a solute (the peptide) and a solvent, whereby the solvent does not interfere with the biological activity of the solute. Suitable solvents include, for example, ethanol, acetic acid and the like.

The term "hydrate" refers to a solvate, as defined hereinabove, where the solvent is water.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Material and Methods

Materials:

Peptides were synthesized by Genemed Synthesis, Inc. (San Francisco, USA). The peptide substrates included p9CREB, ILSRRPS(p)YR (SEQ ID NO:18); pIRS-1, RREGGMSRPAS(p)VDG (SEQ ID NO:19); and PGS-1, YRRAAVPPSPSLSRHSSPSQS(p)EDEEE (SEQ ID NO:20) as previously described [Ilouz et al. (2006) supra].

Peptide inhibitor L803 KEAPPAPPQS(p)P (SEQ ID NO:4) and the L803-mts (SEQ ID NO:5) in which myristic acid was attached to its N-terminal were described previously [Plotkin et al., 2003, supra].

Other L803 variants were synthesized as described herein.

Anti GSK-3β antibody was obtained from Transduction Laboratory (Lexington, Ky., USA).

Anti-phospho-GSK3 ($Y^{216,}$) was obtained from Upstate Biotechnology (Lake Placid, N.Y., USA).

Anti-phospho-CREB ($S^{129/133}$) was obtained from BioSource International, Inc. (Camarillo, Calif., USA).

CREB antibody was from Cell Signaling Technology (Beverly, Mass., USA).

Anti-phospho-IRS-1 ($S^{332}$) was generated as previously described [Liberman, Z. & Eldar-Finkelman, H. (2005) supra].

Radioactive materials were purchased from NEN PerkinElmer USA.

Plasmids and Mutants:

GSK-3β in the pCMV4 vector was used as the template for mutagenesis. Mutations were generated using QuickChange Site Directed Mutagenesis Kit (Stratagene, La Jolla, Calif., USA) according the manufacturer's protocols. Mutations included replacement of D90, K91, R92, F93, K94, V214 to alanine, F93 to tyrosine, and a triple mutation at residues 91-93. All constructs were sequenced to confirm the presence of desired mutations. The sequences of mutagenic oligonucleotides are available from the inventors upon request.

N'IRS-1 (also termed PTB2) plasmid was previously described [Liberman, Z. & Eldar-Finkelman, H. (2005) supra].

CREB-GFP plasmid was purchased from Clontech (Mountain View, Calif., USA).

Cell Transfections and Protein Partial Purifications:

HEK-293 cells were grown in Dulbecco's Modified Eagle's Medium (DMEM), supplemented with 10% fetal calf serum (FCS), 2 mM glutamine, 100 units/ml penicillin, and 100 μg/ml streptomycin. HEK-293 cells were transiently transfected with indicated constructs, using calcium phosphate method as described [Ilouz et al. (2006) supra]. Cells were lysed in ice-cold buffer G (20 mM Tris-HCl, pH 7.5, 10 mM β-glycerophosphate, 10% glycerol, 1 mM EGTA, 1 mM EDTA, 50 mM NaF, 5 mM sodium pyrophosphate, 0.5 mM orthovanadate, 1 mM benzamidine, 10 μg/ml leupeptin, 5 μg/ml aprotinin, 1 μg/ml pepstatin, and 0.5% Triton X100). Cell extracts were centrifuged for 30 minutes at 15,000×g. Supernatants were collected, and equal amounts of proteins were boiled with SDS sample buffer and subjected to gel electrophoresis (7.5-12% polyacrylamide gel), transferred to nitrocellulose membranes, and immunoblotted with indicated antibodies. For partial purification, cells were lysed in buffer H (20 mM Tris, pH 7.3, 1 mM EGTA, 1 mM EDTA, 1 mM orthovanadate, 25 μg/ml leupeptin, 25 μg/ml aprotinin, and 25 μg/ml pepstatin A, 500 nM microcystine LR, and 0.25% Triton X100). The lysates were centrifuged at 15,000×g. The resulting supernatants were passed through DE-52 (Whatman, Maidstone, England) mini-columns that were equilibrated with buffer H. GSK-3β proteins were eluted with the same buffer containing 0.02 M NaCl. Equal amounts of proteins were used for in vitro kinase assays. In all experiments, GSK-3 mutants were expressed at levels at least 5-fold higher than levels of the endogenous GSK-3β as determined by western blot analysis.

In vitro Kinase Assays:

The GSK-3β proteins (WT or mutants) were incubated with indicated substrate in a reaction mixture (50 mM Tris-HCl, pH 7.3, 10 mM magnesium acetate, and 0.01% β-mercaptoethanol) together with 100 μM $^{32}$P[γ-ATP] (0.5 μCi/assay) for 15 minutes. Reactions were stopped by spotting on p81 paper (Whatman) washed with phosphoric acid, and counted for radioactivity as previously described [Ilouz et al. (2006) supra]. In assays from cells overexpressing GSK-3 proteins, the activity of the endogenous GSK-3 that was determined in cells transfected with the pCMV4 vector was subtracted from the activity values obtained for WT and mutants.

Statistical Analysis:

Data were analyzed with Origin Professional 6.0 software using Student's t-test to compare GSK-3 activity of WT vs mutants or peptides-treatment vs. non treatment. Data were considered significant at $p<0.05$ Molecular Dynamics:

Molecular dynamics (MD) simulations were performed with the program Gromacs [Van Der Spoel et al. (2005) *J. Comput. Chem.* 26, 1701-18] employing the united atoms gromos96 43a1 force field [van Gunsteren et al. (1996). Biomolecular Simulation: The Gromos 96 Manual and User Guide] modified to include phosphorylated residues [www-dotgromacsdotorg/Downloads/User_contributions/Force_fields].

The initial model of the solute (peptide or GSK-3β/peptide complex) was immersed in a cube of water, neutralized and energy minimized. This was followed by a 1 ns MD simulation to equilibrate the water, keeping the non hydrogen atoms of the solute restrained. Next, additional 1 or 2 ns simulation was performed, of the peptide or GSK-3β/peptide complex in water. In the latter case the Cα atoms of GSK-3β were restrained and weak restrains were imposed on the distances between the phosphate oxygens of S10(p) in the peptide and the side chain nitrogen atoms of GSK-3β Arg 96, Arg 180, and Lys 205. Only the last 1 ns of each MD simulation was considered in the analysis of the trajectory (0.5 ns for the free peptides).

Rigid Body Docking:

Rigid body docking was performed with the geometric-electrostatic-hydrophobic version of MolFit [Berchanski et al. (2004) *Proteins* 351, 309-26]. The starting geometry of the GSK-3β/ATP complex was modeled as described before [Ilouz et al. (2006) supra], the starting geometry of the free peptide was the representative conformer of the largest cluster obtained in MD simulation of the free peptide in water. The comprehensive docking scan was followed by a new post-scan filtering procedure that incorporates statistical propensity measures and desolvation energy calculations [Kowalsman & Eisenstein (2009) *Proteins* 77, 297-318]. The filtered models were further screened requesting that S10(p) of the peptide makes contact with the positive cavity on the surface of GSK-3β.

Anchoring Spots Mapping:

Anchoring spots mapping identifies preferred binding positions of amino acid side chains on the surface of a protein [Ben-Shimon and Eisenstein (2010) *J. Mol. Biol.* 402, 259-77]. This procedure was used here to detect amino acids that bind in the GSK-3β surface cavity bordered by loop 89-95 and the P-loop. Only side chains that bind with $\Delta G \leq 3$ Kcal/mol were considered.

Example 1

Defining a Substrate Binding Subsite in GSK-3

The Q89-N95 Segment:

The sequence segment delimited by Gln 89 and Asn 95 (see, SEQ ID NO:2), two residues that were found to participate in GSK-3 substrate binding [Ilouz et al. 2006, supra], forms a loop (termed herein 89-95 loop) that together with the conserved P-loop, defines the borders of a surface cavity.

To further explore the role of the 89-95 loop in GSK-3β substrate binding, each of the amino acid residues within this segment was individually mutated to alanine (see, FIG. 1A). HEK-293 cells were transiently transfected with cDNA constructs expressing wild-type (WT) GSK-3β (SEQ ID NO:1), D90A (SEQ ID NO:6), K91A (SEQ ID NO:7), R92A (SEQ ID NO:8), F93A (SEQ ID NO:9), R94A (SEQ ID NO:10) mutant proteins, as described in the Methods section hereinabove. Cell extracts were subjected to western blot analysis using either anti-GSK-3β or antiphospho-GSK-3 (Tyr 216/Tyr 274 for α or β isoforms respectively) antibodies. Control (C) represents extracts from cells expressing the empty vector.

All the mutants were expressed at levels considerably above that of the endogenous GSK-3β (FIG. 1B, upper panel). Like the wild-type (WT) GSK-3β, the mutants were phosphorylated at Tyr 216 (FIG. 1B, lower panel), indicating that their catalytic activity was not impaired by the mutation, as phosphorylation at Tyr 216 reflects an auto-phosphorylation process [as previously described in Cole et al. (2004) *Biochem. J.* 377, 249-55; and Eldar-Finkelman et al. (1996) *Proc. Natl. Acad. Sci. USA* 93, 10228-10233].

The GSK-3β mutants were partially purified by ion exchange chromatography, and their abilities to phosphorylate peptide substrates were tested in in vitro kinase assays. The substrates were: pIRS-1, p9CREB, and pGS-1, phosphorylated peptides derived from the insulin receptor substrate-1 (IRS-1), cAMP responsive element binding protein (CREB), and glycogen synthase, respectively.

The results are presented in Table 1, as the percentage of substrate phosphorylation (indicated peptides, pIRS-1, p9CREB and pGS-1) obtained with WTGSK-3β which was set to 100%, and are mean of 2-3 independent experiments each performed in duplicates±SEM.

As shown in Table 1, three of the five mutants, R92A, F93A, K94A mutants, impaired the ability to phosphorylate the substrates; that Mutation at Lys 91 enhanced substrate phosphorylation by about 20-30%; and, notably, that mutation at Phe 93 had the most deleterious effect for all substrates, reducing the kinase ability to phosphorylate them by more than 50% (see also FIG. 1C). A similar impact was observed with Q89A and N95A mutants [see, Ilouz et al., 2006, supra].

TABLE 1

| | Substrate phosphorylation (% of WTGSK-3β) | | |
|---|---|---|---|
| Mutant | pIRS-1 | p9CREB | pGS-1 |
| D90A (SEQ ID NO: 6) | 88 ± 15 | 92 ± 21 | 83 ± 2 |
| K91A (SEQ ID NO: 7) | 140 ± 18 | 161 ± 5 | 119 ± 5 |
| R92A (SEQ ID NO: 8) | 60 ± 3 | 49 ± 19 | 41 ± 14 |

TABLE 1-continued

| Mutant | Substrate phosphorylation (% of WTGSK-3β) | | |
|---|---|---|---|
| | pIRS-1 | p9CREB | pGS-1 |
| F93A (SEQ ID NO: 9) | 42 ± 13 | 46 ± 2 | 13 ± 7 |
| K94A (SEQ ID NO: 10) | 52 ± 19 | 71 ± 4 | 19 ± 14 |

FIG. 1C presents the phosphorylation of peptide substrates by F93A mutant. F93A was subjected to in vitro kinase assays with substrates pIRS-1, p9CREB, and PGS-1 as described in the Methods section hereinabove. The percentage of substrate phosphorylation obtained with WT-GSK-3β was defined as 100%, and results are means of 2-3 independent experiments each performed in duplicates±SEM.

Hence, Phe 93 adjoins Gln 89 and Asn 95 as an important substrate binding position. Phe 93 is located at the center of the 89-95 loop, it is highly exposed (81% solvent accessibility) and it faces the substrate binding subsite, facilitating contacts with variety of residues.

The role of Phe 93 in substrate binding by employing a cellular system and protein substrates (i.e., not peptides) was further explored. To this end, the WT-GSK-3β and F93A mutant were expressed in HEK-293 cells together with GSK-3 substrates CREB or N'IRS-1 (the N-terminal region of IRS-1). Because GSK-3 requires pre-phosphorylation of its substrates, the cells were treated with forskolin to enhance CREB phosphorylation via activation of cAMP dependent kinase (PKA), or with phorbol ester (PMA) to enhance N'IRS-1 phosphorylation via activation of protein kinase C (PKC). The phosphorylation of CREB at serine 129, and N'IRS-1 at serine 332 (both GSK-3 phosphorylation sites) was then examined.

Thus, HEK293 cells were co-transfected with WT-GSK-3β or F93A plasmids together with construct coding for CREB. Cells were treated with forskolin (10 μM, 1 hour), and cell extracts were subjected to western blot analysis using anti-phospho CREB (Ser 129/133) antibody, as presented in FIG. 1D. Expression levels of CREB and GSK-3 proteins are indicated. The ratio of pCREB/CREB as calculated from densitometry analysis is shown in FIG. 1E.

Similar assay was conducted using N'IRS-1 cDNA construct instead of CREB, and cells were treated with PMA (100 nM, 30 minutes). Anti-phospho IRS-1 (Ser 332) antibody was used as indicated, and the results are presented in FIG. 1F. Expression levels of N'IRS-1 and GSK-3β are indicated. The ratio of pN'IRS-1/N'IRS-1 as calculated from densitometry analysis is shown in FIG. 1G. Results are means of three independent experiments±SEM.

Unlike WT-GSK-3β, expression of F93A did not enhance the phosphorylation of these substrates as determined by specific anti-phospho-antibodies (see, FIGS. 1D-1G). This substantiated the in vitro results showing that Phe 93 interacts with GSK-3 substrates in cellular conditions.

The Role of Phe 93 in the Inhibition of GSK-3 by the Substrate Competitive Inhibitor L803-mts:

Purified GSK-3β was subjected to in vitro kinase assays using pIRS-1, p9CREB, and pGS-1 substrate in the presence or absence of L803-mts (100 μM). As shown in FIG. 2A, L803-mts (SEQ ID NO:5) competes with various substrates, indicating that its binding mode with GSK-3 may share similar interactions to those of GSK-3 substrates.

The interaction of L803-mts and of L803 with the 89-95 loop was thus examined. In vitro kinase assays were performed with WT-GSK-3β and GSK-3β-mutants in the presence or absence of L803-mts (SEQ ID NO:5) or L803 (SEQ ID NO:4). The results are presented in FIGS. 2B and 2C and present the percentages of substrate phosphorylation obtained with the inhibitor versus phosphorylation without the inhibitor (define as 100%), and are means of 2-3 independent experiments±SEM.

The results indicated that L803-mts did not inhibit F93A, yet was able to inhibit all other mutants including Q89A, N95A, R92A, K94A and F93Y (data not shown). Collectively, the results suggest that both L803-mts and L803 and the GSK-3 substrates interact with Phe 93, but, unlike the gsk-3 substrates, L803-mts and L803 do not interact with other residues within the 89-95 loop, including Gln 89 and Asn 95.

Example 2

Novel Modifications of GSK-3 Peptide Inhibitors

Replacing Polar or Charged Amino Acid Residues with Hydrophobic Residues Increases Inhibition Activity:

In view of the fact that Gln 89 and Asn 95 did not contribute to binding of L803 or L803-mts to the catalytic site of GSK-3, the involvement of hydrophilic interactions in the GSK-3 binding site was tested.

L803 includes two charged amino acids Lys1 and Glu2, and a polar residue, Gln9 (see, SEQ ID NO:4). Thus, novel peptide variants were synthesized, in which each of these residues, Lys 1, Glu2 and Gln9, was individually replaced by alanine. These novel variants are termed herein PK1A (where Lys1 was replaced by alanine; SEQ ID NO:11)), PE2A (where Glu2 was replaced by alanine; SEQ ID NO:12), and PQ9A (where Gln9 was replaced by alanine; SEQ ID NO:13). These modification to the sequence of the L803 peptide are shown in FIG. 3A, where the positions that were changed to alanine (residues 1, 2 and 9) and the substitutions of Gln9, are marked bold.

The ability of each peptide to inhibit GSK-3β was then determined by in vitro kinase assays as described hereinabove. Substrate phosphorylation obtained in reaction with no inhibitor was defined as 100% (Con), and the results presented are means of two independent experiments each performed in duplicate±SEM.

As shown in FIG. 3B, PK1A (SEQ ID NO:11) inhibited WT-GSK-3β to a similar extent as L803, but inhibition by PE2A (SEQ ID NO:12) was slightly impaired. In contrast, PQ9A (SEQ ID NO:13), in which Gln 9 was replaced by alanine, increased the inhibition by about two-fold relative to L803.

To further understand the contribution of position 9 to L803 function, Gln 9was replaced with either the charged amino acid arginine (PQ9R; SEQ ID NO:14), or the aromatic residue tyrosine (PQ9Y; SEQ ID NO:15). The results are presented in FIG. 3C and show that both replacements produced non-inhibitory L803 variants.

It therefore appears that the binding of L803 to GSK-3β is mostly mediated by hydrophobic interactions.

Another variant of L803 was designed based on the experimental results for PQ9A. Assuming that the multi proline composition of L803 and its hydrophobic nature dominate the binding to GSK-3β, Gln 9 was replaced by proline, which is a small hydrophobic residue (PQ9P; SEQ ID NO:16). In vitro kinase assays were performed with GSK-3β in the presence of L803 or PQ9P (200 μM each) and the results are presented in FIG. 4. Substrate phosphorylation obtained without inhibitor was defined as 100%, and results are means of two independent experiments±SEM.

Indeed, PQ9P inhibited GSK-3β by about 80% more compared to L803.

The binding of PQ9P to GSK-3 substrate binding site was further demonstrated by MD simulation, and proved supportive to its high binding efficacy (data not shown). MD stimulation of free PQ9P in water showed limited mobility (RMSD<1.5 Å for the last 0.3 ns of the trajectory); it also showed that the peptide adopts a different conformation than L803 (data not shown). Simulation of the GSK-3β/PQ9P complex, starting with PQ9P near the deep groove, showed that the bound PQ9P differs considerably from the free peptide (RMSD deviation of 5.3 Å for the non hydrogen atoms). Hence, the rigidity of this peptide does not help to lower the entropy barrier for binding. The high affinity of PQ9P can be attributed to the extensive contacts with Phe 93, Phe 67 and the substrate binding subsite. PQ9P does not interact with the hydrophobic patch formed by V214, I217 and Y216; hence its binding resembles that of a substrate.

FIG. 5 presents comparative plots showing the inhibition activity of L803, PQ9A and PQ9P, and clearly shows the enhanced inhibition activity of PQ9P.

Modified Peptides having Attached thereto a Fatty Acid Hydrophobic Moiety:

In order to design a cell permeable variant of PQ9P, a fatty acid moiety was attached to its N-terminus was prepared and tested. Myristic acid, as an exemplary fatty acid, was attached to PQ9P via a glycine bridge. The resulting peptide was named L806-mts and had the following amino acid sequence:

```
Myr-GKEAPPAPPPS(p)P      (SEQ ID NO: 17)
```

In vitro kinase assays were performed with GSK-3β in the presence of L803-mts (SEQ ID NO:5) or L806-mts (SEQ ID NO:16) at increasing concentrations and the results are presented in FIG. 6A. Substrate phosphorylation obtained without inhibitor was defined as 100%, and results are means of two independent experiments±SEM.

Indeed, L806-mts inhibited GSK-3β with $IC_{50}$ of about 1 μm.

In further studies, COS-7 cells were treated with L806-mts at various concentrations for 5 hour. Levels of β-catenin were determined by Western blot analysis using anti-β-catenin antibody, as presented in FIG. 6B. Elevation of β-catenin reflects inhibition of GSK-3.

L806-mts-treated COS-7 cells were also tested for phosphorylation of the GSK-3 substrate heat shock factor-1 (HSF-1). Phosphorylation of HSF-1 was determined by Western blot analysis using anti phosphor-HSF-1 antibody, as presented in FIG. 6C. Reduced phosphorylation proves inhibition of GSK-3.

Example 3

In vivo Studies

C57BL/6J mice (12 week old; obtained from Animal Facilities at Tel Aviv University) were treated with L803-mts or L806-mts via a nasal administration (60 μg peptide/per mouse/per day) for 3 days. Non-treated animals served as control. Brains were removed and hippocampus was homogenized in ice-cold 'buffer G'(20 mM Tris pH 7.5, 10 mM β-glycerophosphate, 10% glycerol, 1 mM EGTA, 1 mM EDTA, 50 mM NaF, 5 mM sodium pyrophosphate, 0.5 mM orthovanadate, 1 mM benzamidine, 5 μg/ml leupeptin, 25 μg/ml aprotinin, 5 μg/ml pepstatin, and 0.5% Triton X100). Equal amounts of proteins (50 μg) were subjected to gel electrophoresis, transferred to nitrocellulose membranes, and immunoblotted with anti-β-catenin antibody. Hippocampus β-catenin levels were determined by western blot analysis as described.

The obtained Western Blot analyses are presented in FIG. 7A (for L803-mts and FIG. 7B (for L806-mts). Expression levels of GSK-3β are also shown. As shown in FIGS. 7A and 7B, elevation in β-catenin levels, which is indicative for in vivo inhibition of GSK-3, was seen in the presence of L806-mts.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A peptide having the amino acid sequence I:

$$[Yn \ldots Y_1]ZX_1X_2X_3S(p)[W_1 \ldots Wm] \quad (I)$$

wherein, m equals 1 or 2;

n is 3, 4, 5, 6 or 7, such that said peptide consists of 10 to 13 amino acid residues;

S(p) is a phosphorylated serine residue or a phosphorylated threonine residue;

Z is any amino acid residue excepting serine residue or threonine residue;

$Y_1$-Yn and $W_1$-Wm are each independently any amino acid residue;

each of $X_1$ and $X_2$ is independently a hydrophobic amino acid residue selected from the group consisting of glycine, alanine, leucine, isoleucine, valine, proline, phenylalanine, methionine, cysteine and tryptophan; and $X_3$ is a proline residue.

2. The peptide of claim 1, wherein each of $X_1$ and $X_2$ is independently selected from the group consisting of a proline residue and an alanine residue.

3. The peptide of claim 1, wherein $X_1$ and $X_2$ are each a proline residue.

4. The peptide of claim 1, wherein S(p) is a phosphorylated serine.

5. The peptide of claim 1, wherein Z is an alanine residue.

6. The peptide of claim 1, wherein m is 1 and $W_1$ is a proline residue.

7. The peptide of claim 1, wherein n is 5.

8. The peptide of claim 7, wherein $Y_1$-$Y_5$ has the amino acid sequence Lys-Glu-Ala-Pro-Pro (SEQ ID NO:48).

9. A peptide having an amino acid sequence selected from the group of amino acid sequences as set forth in SEQ ID NOS:11-13 and 16.

10. The peptide of claim 1, consisting of the amino acid sequence as set forth in SEQ ID NO:16.

11. The peptide of claim 1, further comprising a hydrophobic moiety attached thereto.

12. The peptide of claim 11, wherein said hydrophobic moiety is selected from the group consisting of a fatty acid and a fatty acid attached to an amino acid residue.

13. The peptide of claim 12, wherein said fatty acid is myristic acid.

14. The peptide of claim 13, consisting of the amino acid sequence as set forth in SEQ ID NO:17.

15. A pharmaceutical composition comprising, as an active ingredient, the peptide of claim 1, and a pharmaceutically acceptable carrier.

16. The pharmaceutical composition of claim 15, being packaged in a packaging material and identified in print, on or in said packaging material, for use in inhibiting an activity of GSK-3.

17. The pharmaceutical composition of claim 15, being packaged in a packaging material and identified in print, on or in said packaging material, for use in the treatment of a biological condition associated with GSK-3 activity.

18. A method of inhibiting an activity of GSK-3, the method comprising contacting cells expressing GSK-3 with an effective amount of the peptide of claim 1.

19. A method of treating a biological condition associated with GSK-3 activity, the method comprising administering to a subject in need thereof a therapeutically effective amount of the peptide of claim 1.

20. The peptide of claim 9, further comprising a hydrophobic moiety attached thereto.

21. The peptide of claim 20, wherein said hydrophobic moiety is selected from the group consisting of a fatty acid and a fatty acid attached to an amino acid residue.

22. A peptide having the amino acid sequence I:

$$[Yn \ldots Y_1]ZX_1X_2X_3S(p)[W_1 \ldots Wm] \quad (I)$$

wherein, m equals 1 or 2;

n is 3, 4, 5, 6 or 7, such that said peptide consists of 10 to 13 amino acid residues;

S(p) is a phosphorylated serine residue or a phosphorylated threonine residue;

Z is any amino acid residue excepting serine residue or threonine residue;

$Y_1$-Yn and $W_1$-Wm are each independently any amino acid residue;

$X_3$ is a hydrophobic amino acid residue selected from the group consisting of glycine, alanine, leucine, isoleucine, valine, proline, phenylalanine, methionine, cysteine and tryptophan; and $X_1$ and $X_2$ are each a proline residue.

23. The peptide of claim 22, wherein S(p) is a phosphorylated serine.

24. The peptide of claim 22, wherein Z is an alanine residue.

25. The peptide of claim 22, wherein m is 1 and $W_1$ is a proline residue.

26. The peptide of claim 22, wherein n is 5.

27. The peptide of claim 22, further comprising a hydrophobic moiety attached thereto.

28. The peptide of claim 27, wherein said hydrophobic moiety is selected from the group consisting of a fatty acid and a fatty acid attached to an amino acid residue.

29. A pharmaceutical composition comprising, as an active ingredient, the peptide of claim 22, and a pharmaceutically acceptable carrier.

30. A method of inhibiting an activity of GSK-3, the method comprising contacting cells expressing GSK-3 with an effective amount of the peptide of claim 22.

31. A method of treating a biological condition associated with GSK-3 activity, the method comprising administering to a subject in need thereof a therapeutically effective amount of the peptide of claim 22.

32. A peptide having the amino acid sequence I:

$$[Yn \ldots Y_1]ZX_1X_2X_3S(p)[W_1 \ldots Wm] \quad (I)$$

wherein, m equals 1 or 2;

n is 5;

S(p) is a phosphorylated serine residue or a phosphorylated threonine residue;

Z is any amino acid residue excepting serine residue or threonine residue;

and $W_1$-Wm are each independently any amino acid residue;

each of $X_1$, $X_2$ and $X_3$ is independently a hydrophobic amino acid residue selected from the group consisting of glycine, alanine, leucine, isoleucine, valine, proline, phenylalanine, methionine, cysteine and tryptophan; and $Y_1$-$Y_5$ has the amino acid sequence Lys-Glu-Ala-Pro-Pro (SEQ ID NO:48).

33. The peptide of claim 32, wherein $X_3$ is selected from the group consisting of a proline residue and an alanine residue.

34. The peptide of claim 32, wherein S(p) is a phosphorylated serine.

35. The peptide of claim 32, wherein Z is an alanine residue.

36. The peptide of claim 32, wherein m is 1 and $W_1$ is a proline residue.

37. The peptide of claim 32, further comprising a hydrophobic moiety attached thereto.

38. The peptide of claim 37, wherein said hydrophobic moiety is selected from the group consisting of a fatty acid and a fatty acid attached to an amino acid residue.

39. A pharmaceutical composition comprising, as an active ingredient, the peptide of claim 32, and a pharmaceutically acceptable carrier.

40. A method of inhibiting an activity of GSK-3, the method comprising contacting cells expressing GSK-3 with an effective amount of the peptide of claim 32.

41. A method of treating a biological condition associated with GSK-3 activity, the method comprising administering to a subject in need thereof a therapeutically effective amount of the peptide of claim 32.

42. A peptide having the amino acid sequence I:

$$[Yn \ldots Y_1]ZX_1X_2X_3S(p)[W_1 \ldots Wm] \quad (I)$$

wherein, m equals 1 or 2;

n is 3, 4, 5, 6 or 7, such that said peptide consists of 10 to 13 amino acid residues;

S(p) is a phosphorylated serine residue or a phosphorylated threonine residue;

Z is any amino acid residue excepting serine residue or threonine residue;

$Y_1$-Yn and $W_1$-Wm are each independently any amino acid residue; and each of $X_1$, $X_2$ and $X_3$ is independently a hydrophobic amino acid residue selected from the group consisting of glycine, alanine, leucine, isoleucine, valine, proline, phenylalanine, methionine, cysteine and tryptophan, the peptide further comprising a hydrophobic moiety attached thereto.

43. The peptide of claim 42, wherein said hydrophobic moiety is selected from the group consisting of a fatty acid and a fatty acid attached to an amino acid residue.

44. The peptide of claim 43, wherein said fatty acid is myristic acid.

45. The peptide of claim 42, wherein $X_3$ is selected from the group consisting of a proline residue and an alanine residue.

46. The peptide of claim 42, wherein $X_3$ is a proline residue.

47. The peptide of claim 42, wherein each of $X_1$ and $X_2$ is independently selected from the group consisting of a proline residue and an alanine residue.

48. The peptide of claim 42, wherein S(p) is a phosphorylated serine.

49. The peptide of claim 42, wherein Z is an alanine residue.

50. The peptide of claim 42, wherein m is 1 and $W_1$ is a proline residue.

51. The peptide of claim 42, wherein n is 5.

52. The peptide of claim 51, wherein $Y_1$-$Y_5$ has the amino acid sequence Lys-Glu-Ala-Pro-Pro (SEQ ID NO:48).

53. A pharmaceutical composition comprising, as an active ingredient, the peptide of claim 42, and a pharmaceutically acceptable carrier.

54. A method of inhibiting an activity of GSK-3, the method comprising contacting cells expressing GSK-3 with an effective amount of the peptide of claim 42.

55. A method of treating a biological condition associated with GSK-3 activity, the method comprising administering to a subject in need thereof a therapeutically effective amount of the peptide of claim 42.

* * * * *

SEQUENCE LISTING

```
<160> NUMBER OF SEQ ID NOS: 49

<210> SEQ ID NO 1
<211> LENGTH: 433
<212> TYPE: PRT
<213> ORGANISM: Homo sapiens

<400> SEQUENCE: 1

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45
```

```
Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Asp
    290                 295                 300

Ser Ser Gly Thr Gly His Phe Thr Ser Gly Val Arg Val Phe Arg Pro
305                 310                 315                 320

Arg Thr Pro Pro Glu Ala Ile Ala Leu Cys Ser Arg Leu Leu Glu Tyr
                325                 330                 335

Thr Pro Thr Ala Arg Leu Thr Pro Leu Glu Ala Cys Ala His Ser Phe
            340                 345                 350

Phe Asp Glu Leu Arg Asp Pro Asn Val Lys Leu Pro Asn Gly Arg Asp
        355                 360                 365

Thr Pro Ala Leu Phe Asn Phe Thr Thr Gln Glu Leu Ser Ser Asn Pro
    370                 375                 380

Pro Leu Ala Thr Ile Leu Ile Pro Pro His Ala Arg Ile Gln Ala Ala
385                 390                 395                 400

Ala Ser Thr Pro Thr Asn Ala Thr Ala Ala Ser Asp Ala Asn Thr Gly
                405                 410                 415

Asp Arg Gly Gln Thr Asn Asn Ala Ala Ser Ala Ser Ala Ser Asn Ser
            420                 425                 430

Thr
```

<210> SEQ ID NO 2
<211> LENGTH: 7
<212> TYPE: PRT
<213> ORGANISM: Homo sapiens

<220> FEATURE:
<221> NAME/KEY: misc_feature
<223> OTHER INFORMATION: GSK-3 beta loop corresponding to amino acid residues 89-95

<400> SEQUENCE: 2

Gln Asp Lys Arg Phe Lys Asn
1               5

<210> SEQ ID NO 3
<211> LENGTH: 5
<212> TYPE: PRT
<213> ORGANISM: Artificial sequence
<220> FEATURE:
<223> OTHER INFORMATION: GSK-3 recognition motif
<220> FEATURE:
<221> NAME/KEY: misc_feature
<222> LOCATION: (1)..(1)
<223> OTHER INFORMATION: Can be Serine or Threonine
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (2)..(4)
<223> OTHER INFORMATION: Can be any amino acid
<220> FEATURE:
<221> NAME/KEY: misc_feature
<222> LOCATION: (5)..(5)
<223> OTHER INFORMATION: Can be Serine or Threonine
<220> FEATURE:
<221> NAME/KEY: misc_feature
<222> LOCATION: (5)..(5)
<223> OTHER INFORMATION: A phosphorylated residue

<400> SEQUENCE: 3

Xaa Xaa Xaa Xaa Xaa
1               5

<210> SEQ ID NO 4
<211> LENGTH: 11
<212> TYPE: PRT
<213> ORGANISM: Artificial sequence
<220> FEATURE:
<223> OTHER INFORMATION: Substrate competitive inhibitor, L803
<220> FEATURE:
<221> NAME/KEY: misc_feature
<222> LOCATION: (10)..(10)
<223> OTHER INFORMATION: A phosphorylated residue

<400> SEQUENCE: 4

Lys Glu Ala Pro Pro Ala Pro Pro Gln Ser Pro
1               5                   10

<210> SEQ ID NO 5
<211> LENGTH: 12
<212> TYPE: PRT
<213> ORGANISM: Artificial sequence
<220> FEATURE:
<223> OTHER INFORMATION: Substrate competitive inhibitor, L803-mts
<220> FEATURE:
<221> NAME/KEY: misc_feature
<223> OTHER INFORMATION: N- terminally myristoylated
<220> FEATURE:
<221> NAME/KEY: misc_feature
<222> LOCATION: (11)..(11)
<223> OTHER INFORMATION: A phosphorylated residue

<400> SEQUENCE: 5

Gly Lys Glu Ala Pro Pro Ala Pro Pro Gln Ser Pro
1               5                   10

<210> SEQ ID NO 6
<211> LENGTH: 433
<212> TYPE: PRT
<213> ORGANISM: Artificial sequence
<220> FEATURE:
<223> OTHER INFORMATION: GSK-3 beta, D90A mutant

<400> SEQUENCE: 6

```
Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Ala Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Asp
    290                 295                 300

Ser Ser Gly Thr Gly His Phe Thr Ser Gly Val Arg Val Phe Arg Pro
305                 310                 315                 320

Arg Thr Pro Pro Glu Ala Ile Ala Leu Cys Ser Arg Leu Leu Glu Tyr
                325                 330                 335

Thr Pro Thr Ala Arg Leu Thr Pro Leu Glu Ala Cys Ala His Ser Phe
            340                 345                 350

Phe Asp Glu Leu Arg Asp Pro Asn Val Lys Leu Pro Asn Gly Arg Asp
        355                 360                 365
```

```
Thr Pro Ala Leu Phe Asn Phe Thr Thr Gln Glu Leu Ser Ser Asn Pro
    370                 375                 380

Pro Leu Ala Thr Ile Leu Ile Pro Pro His Ala Arg Ile Gln Ala Ala
385                 390                 395                 400

Ala Ser Thr Pro Thr Asn Ala Thr Ala Ala Ser Asp Ala Asn Thr Gly
                405                 410                 415

Asp Arg Gly Gln Thr Asn Asn Ala Ala Ser Ala Ser Ala Ser Asn Ser
            420                 425                 430

Thr


<210> SEQ ID NO 7
<211> LENGTH: 433
<212> TYPE: PRT
<213> ORGANISM: Artificial sequence
<220> FEATURE:
<223> OTHER INFORMATION: GSK-3 beta, K91A mutant

<400> SEQUENCE: 7

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Ala Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285
```

```
Thr Glu Phe Lys Phe Pro Gln Ile Lys Ala His Pro Trp Thr Lys Asp
    290                 295                 300

Ser Ser Gly Thr Gly His Phe Thr Ser Gly Val Arg Val Phe Arg Pro
305                 310                 315                 320

Arg Thr Pro Pro Glu Ala Ile Ala Leu Cys Ser Arg Leu Leu Glu Tyr
                325                 330                 335

Thr Pro Thr Ala Arg Leu Thr Pro Leu Glu Ala Cys Ala His Ser Phe
            340                 345                 350

Phe Asp Glu Leu Arg Asp Pro Asn Val Lys Leu Pro Asn Gly Arg Asp
        355                 360                 365

Thr Pro Ala Leu Phe Asn Phe Thr Thr Gln Glu Leu Ser Ser Asn Pro
    370                 375                 380

Pro Leu Ala Thr Ile Leu Ile Pro Pro His Ala Arg Ile Gln Ala Ala
385                 390                 395                 400

Ala Ser Thr Pro Thr Asn Ala Thr Ala Ala Ser Asp Ala Asn Thr Gly
                405                 410                 415

Asp Arg Gly Gln Thr Asn Asn Ala Ala Ser Ala Ser Ala Ser Asn Ser
            420                 425                 430

Thr


<210> SEQ ID NO 8
<211> LENGTH: 433
<212> TYPE: PRT
<213> ORGANISM: Artificial sequence
<220> FEATURE:
<223> OTHER INFORMATION: GSK-3 beta, R92A mutant

<400> SEQUENCE: 8

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Ala Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
```

```
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Asp
    290                 295                 300

Ser Ser Gly Thr Gly His Phe Thr Ser Gly Val Arg Val Phe Arg Pro
305                 310                 315                 320

Arg Thr Pro Pro Glu Ala Ile Ala Leu Cys Ser Arg Leu Leu Glu Tyr
                325                 330                 335

Thr Pro Thr Ala Arg Leu Thr Pro Leu Glu Ala Cys Ala His Ser Phe
            340                 345                 350

Phe Asp Glu Leu Arg Asp Pro Asn Val Lys Leu Pro Asn Gly Arg Asp
        355                 360                 365

Thr Pro Ala Leu Phe Asn Phe Thr Thr Gln Glu Leu Ser Ser Asn Pro
    370                 375                 380

Pro Leu Ala Thr Ile Leu Ile Pro Pro His Ala Arg Ile Gln Ala Ala
385                 390                 395                 400

Ala Ser Thr Pro Thr Asn Ala Thr Ala Ala Ser Asp Ala Asn Thr Gly
                405                 410                 415

Asp Arg Gly Gln Thr Asn Asn Ala Ala Ser Ala Ser Ala Ser Asn Ser
            420                 425                 430

Thr


<210> SEQ ID NO 9
<211> LENGTH: 433
<212> TYPE: PRT
<213> ORGANISM: Artificial sequence
<220> FEATURE:
<223> OTHER INFORMATION: GSK-3 beta, F93A mutant

<400> SEQUENCE: 9

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Ala Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140
```

```
His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Asp
    290                 295                 300

Ser Ser Gly Thr Gly His Phe Thr Ser Gly Val Arg Val Phe Arg Pro
305                 310                 315                 320

Arg Thr Pro Pro Glu Ala Ile Ala Leu Cys Ser Arg Leu Leu Glu Tyr
                325                 330                 335

Thr Pro Thr Ala Arg Leu Thr Pro Leu Glu Ala Cys Ala His Ser Phe
            340                 345                 350

Phe Asp Glu Leu Arg Asp Pro Asn Val Lys Leu Pro Asn Gly Arg Asp
        355                 360                 365

Thr Pro Ala Leu Phe Asn Phe Thr Thr Gln Glu Leu Ser Ser Asn Pro
    370                 375                 380

Pro Leu Ala Thr Ile Leu Ile Pro Pro His Ala Arg Ile Gln Ala Ala
385                 390                 395                 400

Ala Ser Thr Pro Thr Asn Ala Thr Ala Ala Ser Asp Ala Asn Thr Gly
                405                 410                 415

Asp Arg Gly Gln Thr Asn Asn Ala Ala Ser Ala Ser Ala Ser Asn Ser
            420                 425                 430

Thr


<210> SEQ ID NO 10
<211> LENGTH: 433
<212> TYPE: PRT
<213> ORGANISM: Artificial sequence
<220> FEATURE:
<223> OTHER INFORMATION: GSK-3 beta, K94A mutant

<400> SEQUENCE: 10

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60
```

```
Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Ala Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Asp
    290                 295                 300

Ser Ser Gly Thr Gly His Phe Thr Ser Gly Val Arg Val Phe Arg Pro
305                 310                 315                 320

Arg Thr Pro Pro Glu Ala Ile Ala Leu Cys Ser Arg Leu Leu Glu Tyr
                325                 330                 335

Thr Pro Thr Ala Arg Leu Thr Pro Leu Glu Ala Cys Ala His Ser Phe
            340                 345                 350

Phe Asp Glu Leu Arg Asp Pro Asn Val Lys Leu Pro Asn Gly Arg Asp
        355                 360                 365

Thr Pro Ala Leu Phe Asn Phe Thr Thr Gln Glu Leu Ser Ser Asn Pro
    370                 375                 380

Pro Leu Ala Thr Ile Leu Ile Pro Pro His Ala Arg Ile Gln Ala Ala
385                 390                 395                 400

Ala Ser Thr Pro Thr Asn Ala Thr Ala Ala Ser Asp Ala Asn Thr Gly
                405                 410                 415

Asp Arg Gly Gln Thr Asn Asn Ala Ala Ser Ala Ser Ala Ser Asn Ser
            420                 425                 430

Thr
```

<210> SEQ ID NO 11
<211> LENGTH: 11
<212> TYPE: PRT
<213> ORGANISM: Artificial sequence
<220> FEATURE:
<223> OTHER INFORMATION: PK1A synthetic peptide
<220> FEATURE:

<221> NAME/KEY: misc_feature
<222> LOCATION: (10)..(10)
<223> OTHER INFORMATION: A phosphorylated residue

<400> SEQUENCE: 11

Ala Glu Ala Pro Pro Ala Pro Pro Gln Ser Pro
1 5 10

<210> SEQ ID NO 12
<211> LENGTH: 11
<212> TYPE: PRT
<213> ORGANISM: Artificial sequence
<220> FEATURE:
<223> OTHER INFORMATION: PE2A synthetic peptide
<220> FEATURE:
<221> NAME/KEY: misc_feature
<222> LOCATION: (10)..(10)
<223> OTHER INFORMATION: A phosphorylated residue

<400> SEQUENCE: 12

Lys Ala Ala Pro Pro Ala Pro Pro Gln Ser Pro
1 5 10

<210> SEQ ID NO 13
<211> LENGTH: 11
<212> TYPE: PRT
<213> ORGANISM: Artificial sequence
<220> FEATURE:
<223> OTHER INFORMATION: PQ9A synthetic peptide
<220> FEATURE:
<221> NAME/KEY: misc_feature
<222> LOCATION: (10)..(10)
<223> OTHER INFORMATION: A phosphorylated residue

<400> SEQUENCE: 13

Lys Glu Ala Pro Pro Ala Pro Pro Ala Ser Pro
1 5 10

<210> SEQ ID NO 14
<211> LENGTH: 11
<212> TYPE: PRT
<213> ORGANISM: Artificial sequence
<220> FEATURE:
<223> OTHER INFORMATION: PQ9R synthetic peptide
<220> FEATURE:
<221> NAME/KEY: misc_feature
<222> LOCATION: (10)..(10)
<223> OTHER INFORMATION: A phosphorylated residue

<400> SEQUENCE: 14

Lys Glu Ala Pro Pro Ala Pro Pro Arg Ser Pro
1 5 10

<210> SEQ ID NO 15
<211> LENGTH: 11
<212> TYPE: PRT
<213> ORGANISM: Artificial sequence
<220> FEATURE:
<223> OTHER INFORMATION: PQ9Y synthetic peptide
<220> FEATURE:
<221> NAME/KEY: misc_feature
<222> LOCATION: (10)..(10)
<223> OTHER INFORMATION: A phosphorylated residue

<400> SEQUENCE: 15

Lys Glu Ala Pro Pro Ala Pro Pro Tyr Ser Pro
1 5 10

<210> SEQ ID NO 16

<211> LENGTH: 11
<212> TYPE: PRT
<213> ORGANISM: Artificial sequence
<220> FEATURE:
<223> OTHER INFORMATION: PQ9P (L806) synthetic peptide
<220> FEATURE:
<221> NAME/KEY: misc_feature
<222> LOCATION: (10)..(10)
<223> OTHER INFORMATION: A phosphorylated residue

<400> SEQUENCE: 16

Lys Glu Ala Pro Pro Ala Pro Pro Pro Ser Pro
1 5 10

<210> SEQ ID NO 17
<211> LENGTH: 12
<212> TYPE: PRT
<213> ORGANISM: Artificial sequence
<220> FEATURE:
<223> OTHER INFORMATION: PQ9P+myristic acid at the N-terminus (L806-mts) synthetic peptide
<220> FEATURE:
<221> NAME/KEY: misc_feature
<223> OTHER INFORMATION: N- terminally myristoylated
<220> FEATURE:
<221> NAME/KEY: misc_feature
<222> LOCATION: (11)..(11)
<223> OTHER INFORMATION: A phosphorylated residue

<400> SEQUENCE: 17

Gly Lys Glu Ala Pro Pro Ala Pro Pro Pro Ser Pro
1 5 10

<210> SEQ ID NO 18
<211> LENGTH: 9
<212> TYPE: PRT
<213> ORGANISM: Artificial sequence
<220> FEATURE:
<223> OTHER INFORMATION: p9CREB synthetic peptide
<220> FEATURE:
<221> NAME/KEY: misc_feature
<222> LOCATION: (7)..(7)
<223> OTHER INFORMATION: A phosphorylated residue

<400> SEQUENCE: 18

Ile Leu Ser Arg Arg Pro Ser Tyr Arg
1 5

<210> SEQ ID NO 19
<211> LENGTH: 14
<212> TYPE: PRT
<213> ORGANISM: Artificial sequence
<220> FEATURE:
<223> OTHER INFORMATION: pIRS-1 synthetic peptide
<220> FEATURE:
<221> NAME/KEY: misc_feature
<222> LOCATION: (11)..(11)
<223> OTHER INFORMATION: A phosphorylated residue

<400> SEQUENCE: 19

Arg Arg Glu Gly Gly Met Ser Arg Pro Ala Ser Val Asp Gly
1 5 10

<210> SEQ ID NO 20
<211> LENGTH: 26
<212> TYPE: PRT
<213> ORGANISM: Artificial sequence
<220> FEATURE:
<223> OTHER INFORMATION: PGS-1 synthetic peptide
<220> FEATURE:
<221> NAME/KEY: misc_feature
<222> LOCATION: (21)..(21)
<223> OTHER INFORMATION: A phosphorylated residue

<400> SEQUENCE: 20

Tyr Arg Arg Ala Ala Val Pro Pro Ser Pro Ser Leu Ser Arg His Ser
1 5 10 15

Ser Pro Ser Gln Ser Glu Asp Glu Glu Glu
20 25

<210> SEQ ID NO 21
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (5)..(5)
<223> OTHER INFORMATION: A phosphorylated residue

<400> SEQUENCE: 21

Ala Pro Pro Pro Ser
1 5

<210> SEQ ID NO 22
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (5)..(5)
<223> OTHER INFORMATION: A phosphorylated residue

<400> SEQUENCE: 22

Ala Pro Pro Pro Thr
1 5

<210> SEQ ID NO 23
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (5)..(5)
<223> OTHER INFORMATION: A phosphorylated residue

<400> SEQUENCE: 23

Ala Ala Pro Pro Ser
1 5

<210> SEQ ID NO 24
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (5)..(5)
<223> OTHER INFORMATION: A phosphorylated residue

<400> SEQUENCE: 24

Ala Ala Pro Pro Thr
1 5

<210> SEQ ID NO 25
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (5)..(5)
<223> OTHER INFORMATION: A phosphorylated residue

<400> SEQUENCE: 25

Ala Ala Ala Pro Ser
1 5

<210> SEQ ID NO 26
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (5)..(5)
<223> OTHER INFORMATION: A phosphorylated residue

<400> SEQUENCE: 26

Ala Ala Ala Pro Thr
1 5

<210> SEQ ID NO 27
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (5)..(5)
<223> OTHER INFORMATION: A phosphorylated residue

<400> SEQUENCE: 27

Ala Pro Ala Pro Ser
1 5

<210> SEQ ID NO 28
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (5)..(5)
<223> OTHER INFORMATION: A phosphorylated residue

<400> SEQUENCE: 28

Ala Pro Ala Pro Thr
1 5

<210> SEQ ID NO 29
<211> LENGTH: 5

<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (5)..(5)
<223> OTHER INFORMATION: A phosphorylated residue

<400> SEQUENCE: 29

Ala Gly Pro Pro Ser
1 5

<210> SEQ ID NO 30
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (5)..(5)
<223> OTHER INFORMATION: A phosphorylated residue

<400> SEQUENCE: 30

Ala Gly Pro Pro Thr
1 5

<210> SEQ ID NO 31
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (5)..(5)
<223> OTHER INFORMATION: A phosphorylated residue

<400> SEQUENCE: 31

Ala Gly Gly Pro Ser
1 5

<210> SEQ ID NO 32
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (5)..(5)
<223> OTHER INFORMATION: A phosphorylated residue

<400> SEQUENCE: 32

Ala Gly Gly Pro Thr
1 5

<210> SEQ ID NO 33
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (5)..(5)
<223> OTHER INFORMATION: A phosphorylated residue

<400> SEQUENCE: 33

Ala Pro Gly Pro Ser
1 5

<210> SEQ ID NO 34
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (5)..(5)
<223> OTHER INFORMATION: A phosphorylated residue

<400> SEQUENCE: 34

Ala Pro Gly Pro Thr
1 5

<210> SEQ ID NO 35
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (2)..(2)
<223> OTHER INFORMATION: Can be Leu or Ile
<220> FEATURE:
<221> NAME/KEY: misc_feature
<222> LOCATION: (5)..(5)
<223> OTHER INFORMATION: A phosphorylated residue

<400> SEQUENCE: 35

Ala Xaa Pro Pro Ser
1 5

<210> SEQ ID NO 36
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (2)..(2)
<223> OTHER INFORMATION: can be Leu or Ile
<220> FEATURE:
<221> NAME/KEY: misc_feature
<222> LOCATION: (2)..(2)
<223> OTHER INFORMATION: Can be Leu or Ile
<220> FEATURE:
<221> NAME/KEY: misc_feature
<222> LOCATION: (5)..(5)
<223> OTHER INFORMATION: A phosphorylated residue

<400> SEQUENCE: 36

Ala Xaa Pro Pro Thr
1 5

<210> SEQ ID NO 37
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (2)..(3)
<223> OTHER INFORMATION: Can be Leu or Ile
<220> FEATURE:
<221> NAME/KEY: misc_feature
<222> LOCATION: (5)..(5)
<223> OTHER INFORMATION: A phosphorylated residue

<400> SEQUENCE: 37

Ala Xaa Xaa Pro Ser
1               5

<210> SEQ ID NO 38
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (2)..(3)
<223> OTHER INFORMATION: Can be Leu or Ile
<220> FEATURE:
<221> NAME/KEY: misc_feature
<222> LOCATION: (5)..(5)
<223> OTHER INFORMATION: A phosphorylated residue

<400> SEQUENCE: 38

Ala Xaa Xaa Pro Thr
1               5

<210> SEQ ID NO 39
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (3)..(3)
<223> OTHER INFORMATION: Can be Leu or Ile
<220> FEATURE:
<221> NAME/KEY: misc_feature
<222> LOCATION: (5)..(5)
<223> OTHER INFORMATION: A phosphorylated residue

<400> SEQUENCE: 39

Ala Pro Xaa Pro Ser
1               5

<210> SEQ ID NO 40
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (3)..(3)
<223> OTHER INFORMATION: Can be Leu or Ile
<220> FEATURE:
<221> NAME/KEY: misc_feature
<222> LOCATION: (5)..(5)
<223> OTHER INFORMATION: A phosphorylated residue

<400> SEQUENCE: 40

Ala Pro Xaa Pro Thr
1 5

<210> SEQ ID NO 41
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (5)..(5)
<223> OTHER INFORMATION: A phosphorylated residue

<400> SEQUENCE: 41

Ala Val Pro Pro Ser
1 5

<210> SEQ ID NO 42
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (5)..(5)
<223> OTHER INFORMATION: A phosphorylated residue

<400> SEQUENCE: 42

Ala Val Pro Pro Thr
1 5

<210> SEQ ID NO 43
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (5)..(5)
<223> OTHER INFORMATION: A phosphorylated residue

<400> SEQUENCE: 43

Ala Val Val Pro Ser
1 5

<210> SEQ ID NO 44
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (5)..(5)
<223> OTHER INFORMATION: A phosphorylated residue

<400> SEQUENCE: 44

Ala Val Val Pro Thr
1 5

<210> SEQ ID NO 45
<211> LENGTH: 5

<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (5)..(5)
<223> OTHER INFORMATION: A phosphorylated residue

<400> SEQUENCE: 45

```
Ala Pro Val Pro Ser
1               5
```

<210> SEQ ID NO 46
<211> LENGTH: 5
<212> TYPE: PRT
<213> ORGANISM: Artificial sequence
<220> FEATURE:
<223> OTHER INFORMATION: An exemplary portion of the peptide describe in the preferred embodiments
<220> FEATURE:
<221> NAME/KEY: misc_feature
<222> LOCATION: (5)..(5)
<223> OTHER INFORMATION: A phosphorylated residue

<400> SEQUENCE: 46

```
Ala Pro Val Pro Thr
1               5
```

<210> SEQ ID NO 47
<211> LENGTH: 433
<212> TYPE: PRT
<213> ORGANISM: Artificial sequence
<220> FEATURE:
<223> OTHER INFORMATION: GSK-3 beta, V214A mutant

<400> SEQUENCE: 47

```
Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190
```

```
Thr Ala Val Leu Lys Leu Cys Asp Phe Gly Ser Ala Lys Gln Leu Val
        195                 200                 205

Arg Gly Glu Pro Asn Ala Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Asp
    290                 295                 300

Ser Ser Gly Thr Gly His Phe Thr Ser Gly Val Arg Val Phe Arg Pro
305                 310                 315                 320

Arg Thr Pro Pro Glu Ala Ile Ala Leu Cys Ser Arg Leu Leu Glu Tyr
                325                 330                 335

Thr Pro Thr Ala Arg Leu Thr Pro Leu Glu Ala Cys Ala His Ser Phe
            340                 345                 350

Phe Asp Glu Leu Arg Asp Pro Asn Val Lys Leu Pro Asn Gly Arg Asp
        355                 360                 365

Thr Pro Ala Leu Phe Asn Phe Thr Thr Gln Glu Leu Ser Ser Asn Pro
    370                 375                 380

Pro Leu Ala Thr Ile Leu Ile Pro Pro His Ala Arg Ile Gln Ala Ala
385                 390                 395                 400

Ala Ser Thr Pro Thr Asn Ala Thr Ala Ala Ser Asp Ala Asn Thr Gly
                405                 410                 415

Asp Arg Gly Gln Thr Asn Asn Ala Ala Ser Ala Ser Ala Ser Asn Ser
            420                 425                 430

Thr


<210> SEQ ID NO 48
<211> LENGTH: 5
<212> TYPE: PRT
<213> ORGANISM: Artificial sequence
<220> FEATURE:
<223> OTHER INFORMATION: An exemplary portion of the peptide describe in
      the preferred embodiments

<400> SEQUENCE: 48

Lys Glu Ala Pro Pro
1               5


<210> SEQ ID NO 49
<211> LENGTH: 10
<212> TYPE: PRT
<213> ORGANISM: Homo sapiens
<220> FEATURE:
<221> NAME/KEY: misc_feature
<223> OTHER INFORMATION: corresponding to amino acid residues 88-97 of
      GSK-3 beta

<400> SEQUENCE: 49

Leu Gln Asp Lys Arg Phe Lys Asn Arg Glu
1               5                   10
```